US007060460B2

(12) United States Patent
Necina et al.

(10) Patent No.: US 7,060,460 B2
(45) Date of Patent: Jun. 13, 2006

(54) METHOD FOR RECONSTITUTING A RECOMBINANT PROTEIN TO ITS BIOLOGICALLY ACTIVE FORM

(75) Inventors: Roman Necina, Vienna (AT); Robert Schlegl, Vienna (AT); Alois Jungbauer, Vienna (AT); Christine Machold, Vienna (AT)

(73) Assignee: Boehringer Ingelheim Austria GmbH, Vienna (AT)

( * ) Notice: Subject to any disclaimer, the term of this patent is extended or adjusted under 35 U.S.C. 154(b) by 0 days.

(21) Appl. No.: 10/261,508

(22) Filed: Oct. 2, 2002

(65) Prior Publication Data

US 2003/0113866 A1 Jun. 19, 2003

Related U.S. Application Data

(60) Provisional application No. 60/330,463, filed on Oct. 22, 2001.

(30) Foreign Application Priority Data

Oct. 3, 2001 (EP) .................................. 01123698

(51) Int. Cl.
*C12P 21/06* (2006.01)
(52) U.S. Cl. ..................................... 435/69.1; 530/417
(58) Field of Classification Search ................ 530/415, 530/416, 417, 820, 408, 409; 435/69.7, 69.1
See application file for complete search history.

(56) References Cited

U.S. PATENT DOCUMENTS 4,977,248 A * 12/1990 Creighton ................... 530/412

OTHER PUBLICATIONS

Altamirano, M.M., et al., "Refolding chromatography with immobilized mini-chaperones," *Proc. Natl. Acad. Sci. USA* 94:3576-3578, National Academy of Sciences (1997).
Altamirano, M.M., et al., "Oxidative refolding chromatography: folding of the scorpion toxin Cn5," *Nat. Biotech.* 17:187-191, Nature America Inc. (1999).
Begovich, J.M., et al., "A High-Capacity Pressurized Continuous Chromatograph," *Sep. Sci. Tech.* 18:1167-1191, Marcel Dekker, Inc. (1983).
Begovich, J.M., and Sisson, W.G., "A Rotating Annular Chromatograph for Continuous Separations," *AIChE J.* 30:705-710, American Institute of Chemical Engineers (1984).
Bloomingburg, G.F., et al., "Continuous Separation of Proteins by Annular Chromatography," *Ind. Eng. Chem. Res.* 30:1061-1067, American Chemical Society (1991).
Bloomingburg, G.F., and Carta, G., "Separation of protein mixtures by continuous annular chromatography with step elution," *Chem. Eng. J.* 55:B19-B27, Elsevier Science S.A. (1994).
Boismenu, R., et al., "Purification and Characterization of Human and Mouse Recombinant Alpha-Fetoproteins Expressed in *Escherichia coli*," *Prot. Express. Purif.* 10:10-26, Academic Press (1997).
Broughton, D.B., "Production-Scale Adsorptive Separations of Liquid Mixtures by Simulated Moving-Bed Technology," *Sep. Sci. Tech.* 19:723-736, Marcel Dekker, Inc. (1984-85).
Buchacher, A., et al., "Continuous Removal of Protein Aggregates by Annular Chromatography," *Biotechnol. Prog.* 17:140-149, American Chemical Society and American Institute of Chemical Engineers (Jan./Feb. 2001).
Buchner, J., and Rudolph, R., "Routes to active proteins from transformed microorganisms," *Curr. Opin. Biotechnol.* 2:532-538, Current Biology Ltd. (1991).
Buchner, J., et al., "Renaturation of a Single-Chain Immunotoxin Facilitated by Chaperones and Protein Disulfide Isomerase," *Bio/Technol.* 10:682-685, Nature Publishing Co. (1992).
Byers, C.H., et al., "Pilot-Scale Studies of Sugar Separations by Continuous Chromatography," *Appl. Biochem. Biotech.* 20/21:635-654, The Humana Press, Inc. (1989).
Byers, C.H., et al., "Sugar Separations on a Pilot Scale by Continuous Annular Chromatography," *Biotechnol. Prog.* 6:13-20, American Chemical Society and American Institute of Chemical Engineers (1990).
Canon, R.M., and Sisson, W.G., "Operation of an Improved, Continuous Annular Chromatograph," *J. Liq. Chrom.* 1:427-441, Marcel Dekker, Inc. (1978).
Canon, R.M., et al., "Pressurized Continuous Chromatography," *Sep. Sci. Tech.* 15:655-678, Marcel Dekker, Inc. (1980).
Carlson, J.D., and Yarmush, M.L., "Antibody Assisted Protein Refolding," *Bio/Technol.* 10:86-91, Nature Publishing Co. (1992).

(Continued)

*Primary Examiner*—Jon Weber
*Assistant Examiner*—Robert B. Mondesi
(74) *Attorney, Agent, or Firm*—Sterne, Kessler, Goldstein & Fox P.L.L.C.

(57) ABSTRACT

In a method for reconstituting a recombinant protein from a denatured state to its active form, a feed solution containing the recombinant protein in its denatured and/or in biologically inactive intermediate forms is subjected to a chromatographic separation process, in which the protein is reconstituted under conditions that promote refolding of the protein and the intermediate forms are separated from the refolded protein. The denatured form and/or the inactive intermediate forms of the protein are separated from the refolded protein in a continuous or quasi-continuous manner and optionally recycled to the feed solution.

33 Claims, 12 Drawing Sheets

OTHER PUBLICATIONS

Carta, G., et al., "Separation of Metals by Continuous Annular Chromatography with Step Elution," *Chem. Eng. Comm.* 79:207-227, Gordon and Breach Science Publishers S.A. (1989).

Carta, G., and Byers, C.H., "Novel Applications of Continuous Annular Chromatography," in *New Directions in Sorption Technology*, Keller II, G.E., and Yang, R.T., Eds., Butterworth Publishers, Stoneham, MA, pp. 167-179 (1989).

Dalvie, S.K., et al., "Mathematical Model of a Rotating Annular Continuous Size Exclusion Chromatograph," in *Downstream Processing and Bioseparation: Recovery and Purification of Biological Products*, Hamel, J-F.P, et al., Eds., American Chemical Society, Washington, DC, pp. 268-284 (1990).

De Bernardez Clark, E., et al., "Inhibition of Aggregation Side Reactions during in Vitro Protein Folding," *Meth. Enzymol.* 309:217-236, Academic Press (1999).

De Bernardez Clark, E., "Protein refolding for industrial processes," *Curr. Opin. Biotech.* 12:202-207, Elsevier Science Ltd. (Apr. 2001).

Feng, W., et al., "Affinity chromatography of human estrogen receptor-α expressed in *Saccharomyces cerevisiae*. Combination of heparin- and 17β-estradiol-affinity chromatography," *J. Chrom. A.* 852:161-173, Elsevier Science B.V. (1999).

Fox Jr., J.B., et al., "Continuous Chromatography Apparatus. I. Construction," *J. Chromatog.* 43:48-54, Elsevier Publishing Company (1969).

Fox Jr., J.B., "Continuous Chromatography Apparatus. II. Operation," *J. Chromatog.* 43:55-60, Elsevier Publishing Company (1969).

Goto, M., and Goto, S., "Continuous Separation Using an Annular Chromatograph with Rotating Inlet and Outlet," *J. Chem. Eng. Japan* 20:598-603, Society of Chemical Engineers (1987).

Guise, A.D., and Chaudhuri, J.B., "Recovery and Reuse of the Molecular Chaperone GroEL for In Vitro Protein Refolding," *Biotechnol. Prog.* 14:343-346, American Chemical Society and American Institute of Chemical Engineers (1998).

Halenbeck, R., et al., "Renaturation and Purifcation of Biologically Active Recombinant Human Macrophage Colony-Stimulating Factor Expressed in *E. coli*," *Bio/Technol.* 7:710-715, Nature Publishing Co. (1989).

Heuer, C., et al., "Vergleich verschiedener verfahrenstechnischer Konzepte der präparativen Flüssigchromatograhie," *Chemie Ingenieur Technik* 69:1535-1546, VCH Verlagsgesellschaft mbH (1997).

Hidajat, K., et al., "Simulated counter-current adsorption processes: a theoretical analysis of the effect of subdividing the adsorbent bed," *Chem. Eng. Sci.* 41:2953-2956, Pergamon Journals Ltd. (1986).

Horwich, A.L., et al., "Protein-catalyzed protein folding," *Trends Biotech.* 8:126-131, Elsevier Trends Journals (1990).

Jäger, M., and Plückthun, A., "The rate-limiting steps for the folding of an antibody scFv fragment," *FEBS Lett.* 418:106-110, Elsevier Science B.V. (1997).

Kane, J.F., and Hartley, D.L., "Formation of recombinant protein inclusion bodies in *Escherichia coli*," *Trends. Biotech.* 6:95-101, Elsevier Publications, Cambridge (1988).

Katoh, S., and Katoh, Y., "Continuous refolding of lysozyme with fed-batch addition of denatured protein solution," *Process Biochemistry* 35:1119-1124, Elsevier Science Ltd. (Jul. 2000).

Kiefhaber, T., et al., "Protein Aggregation *in Vitro* and *in Vivo*: A Quantitative Model of the Kinetic Competition Between Folding and Aggregation," *Bio/Technol.* 9:825-829, Nature Publishing Co. (1991).

Kitakawa, A., et al., "Modeling and Simulation of Continuous Rotating Annular Ion-Exchange Chromatography for Separation of Amino Acids," *Sep. Sci. Tech.* 30:3089-3110, Marcel Dekker, Inc. (1995).

Kitakawa, A., et al., "Complete Separation of Amino Acids Using Continuous Rotating Annular Ion Exchange Chromatography with Partial Recycle of Effluent," *Ind. Eng. Chem. Res.* 36:3809-3814, American Chemical Society (1997).

Kohler, R.J., et al., "Design of a Molecular Chaperone-Assisted Protein Folding Bioreactor," *Biotechnol. Prog.* 16:671-675, American Chemical Society and American Institute of Chemical Engineers (Jul. 2000).

Lilie, H., et al., "Prolyl isomerases catalyze antibody folding in vitro," *Prot. Sci.* 2:1490-1496, Cambridge University Press (1993).

Lilie, H., et al., "Advances in refolding of proteins produced in *E. coli*," *Curr. Opin. Biotechnol.* 9:497-501, Current Biology Publications (1998).

Martin, A.J.P., "Summarizing Paper," in *Discussions of the Faraday Society, Chromatographic Analysis, No. 7*, Gurney and Jackson, London, England, pp. 332-336 (1949).

Nicholas, R.A., and Fox, J.B. Jr., "Continuous Chromatography Apparatus. III. Application," *J. Chromatog.* 43:61-65, Elsevier Publishing Company (1969).

Noiva, R., "Enzymatic Catalysis of Disulfide Formation," *Prot. Express. Purif.* 5:1-13, Academic Press, Inc. (1994).

Phadtare, S., et al. "Refolding and release of tubulins by a functional immobilized groEL column," *Biochim. Biophys. Acta* 1208:189-192, Elsevier Science B.V. (1994).

Preston, N.S., et al., "The production and characterisation of an immobilized chaperonin system," *Biochim. Biophys. Acta* 1426:99-109, Elsevier Science B.V. (1999).

Reissner, K., et al., "Preparative desalting of bovine serum albumin by continuous annular chromatography," *J. Chrom. A.* 763:49-56, *Elsevier Science* (1997).

Schönbrunner, E.R., and Schmid, F.X., "Peptidyl-prolyl *cis-trans* isomerase improves the efficiency of protein disulfide isomerase as a catalyst of protein folding," *Proc. Natl. Acad. Sci. USA* 89:4510-4513, The National Academy of Sciences (1992).

Schulte, M., and Strube, J., "Preparative enantioseparation by simulated moving bed chromatography," *J. Chrom. A.* 906:399-416, Elsevier Science B.V. (Jan. 2001).

Scott, C.D., et al., "Pressurized, Annular Chromatograph for Continuous Separations," *J. Chromatog.* 126:381-400, Elsevier Science B.V. (1976).

Shimizu, H., et al., "Renaturation of Reduced Ribonuclease A with a Microsphere-Induced Refolding System," *Biotechnol. Prog.* 16:248-253, American Chemical Society and American Institute of Chemical Engineers (Published on Web, Mar. 2000).

Sisson, W.G., et al., "Continuous Chromatography," *Chemtech* 18:498-502, American Chemical Society (1988).

Sisson, W.G., et al., "Application of Continuous Annular Chromatography to Size-exclusion Separations," *Prep. Chrom.* 1:139-162, Gordon and Breach Science Publishers, Inc. (1989).

Takahashi, Y., and Goto, S., "Continuous Separation Using an Annular Chromatograph with Non-Isocratic Elution," *J.*

*Chem. Eng. Japan* 24:121-123, Society of Chemical Engineers (1991).

Takahashi, Y., Goto, S., "Continuous Separations of Amino Acids by Using an Annular Chromatograph with Rotating Inlet and Outlet," *Sep. Sci. Tech.* 26:1-13, Marcel Dekker, Inc. (1991).

Takahashi, Y., and Goto, S., "Continuous Concentration of Single Component Using an Annular Chromatograph," *J. Chem. Eng. Japan.* 24:460-465, Society of Chemical Engineers (1991).

Takahashi, Y., and Goto, S., "Continuous Separation and Concentration of Proteins Using an Annular Chromatograph," *J. Chem. Eng. Japan.* 25:403-407, Society of Chemical Engineers (1992).

Takahashi, Y., and Goto, S., "Continuous Separation of Fructooligosaccharides Using an Annular Chromatograph," *Sep. Sci. Tech.* 29:1311-1318, Marcel Dekker, Inc. (1994).

Uretschläger, A., et al., "Continuous separation of green fluorescent protein by annular chromatography," *J. Chrom. A.* 908:243-250, Elsevier Science B.V. (Jan. 2001).

Wolfgang, J., and Prior, A., "Continuous Separation of Carbohydrates by Ion-Exchange Chromatography," *Sep. Sci. Tech.* 32:71-82, Marcel Dekker, Inc. (1997).

Yang, H.-P., et al., "Catalysis of the refolding of urea denatured creatine kinase by peptidyl-prolyl *cis-trans* isomerase," *Biochim. Biophys. Acta. 1338*:147-150, Elsevier Science B.V. (1997).

Yoshii, H., et al., "Refolding of Denatured and Reduced Lysozyme with Cysteine/Cystine Red/Ox Solution in Diafiltration," *J. Chem. Eng. Japan* 34:211-215, Society of Chemical Engineers (Feb. 2001).

* cited by examiner

METHOD FOR RECONSTITUTING A RECOMBINANT PROTEIN TO ITS BIOLOGICALLY ACTIVE FORM

CROSS-REFERENCE TO RELATED APPLICATIONS

This application claims the benefit of U.S. Provisional Application No. 60/330,463, filed Oct. 22, 2001, and European Application No. EP 01 123 698.1, filed Oct. 3, 2001, both of which are hereby incorporated herein by reference.

BACKGROUND OF THE INVENTION

1. Field of the Invention

The invention relates to the field of recombinant protein production.

2. Related Art

Proteins for industrial applications, e.g. for use as biopharmaceuticals or fine chemicals, are either obtained by extraction and purification from a natural source, such as a plant or animal tissue or microorganisms, or by means of recombinant DNA technology.

To produce a recombinant protein, the cDNA encoding the protein of interest is inserted into an expression vector and the recombinant vector is transformed into host cells, which are grown to overexpress the protein. The host cells may be selected from microorganisms such as bacteria, yeast or fungi, or from animal or plant cells.

Overexpression of a protein is a complex event. To obtain the correct conformation, the protein, already in its native state, is associated with so-called "folding helper proteins" and enzymes. The folding helper proteins, also termed "chaperones" or "minichaperones", interact in a complex way so that the protein regains its native conformation after passing through various intermediate states. Some of the intermediate states may be quite stable. Enzymes involved in protein maturation either catalyze the rapid formation of disulfide bridges (Horwich, A. L., et al., *Trends Biotechnol.* 8:126–131 (1990); Noiva, R., *Protein Expr Purif.* 5:1–13 (1994)), the isomerization of prolyl-peptide linkages (Schonbrunner, E. R., et al., *Proc. Natl. Acad. Sci. (USA)* 89:4510–4513 (1992); Lilie, H., et al., *Protein Sci.* 2:1490–1496 (1993); Jager, M., et al., *FEBS Lett.* 418: 106–110 (1997); Yang, H. P., et al., *Biochim Biophys Acta* 1338:147–150 (1997)) or more complex modifications, such as the truncation of the protein, side chain modifications or modifications of the N- and C-terminus. When a protein is efficiently overexpressed, the production of the nascent peptide chain occurs faster than the folding of the protein. For some proteins, an intermediate state may also form aggregates (in the following, the term "intermediate" forms also encompasses aggregate forms).

Overall, aggregate formation occurs much faster than the complete folding of a protein (Kane, J. F. and D. L., H., *TIBTECH* 6:95–100 (1988); Buchner, J. and Rudolph, R., *Current Opinion Biotechnology* 2:532–538 (1991)).

In expression systems, in which such conditions are present, the protein is deposited in the cells in a paracrystalline form, so-called "inclusion bodies", also termed "refractile bodies".

Since the protein, when present in the form of insoluble inclusion bodies, is shielded from enzymatic attack, such as proteolysis, and cannot interfere with the physiology of the cells. Recombinant DNA technology has taken advantage of this aberrant way of protein secretion, e.g. for the production of the proteins that are toxic for the cells.

To obtain a protein from host cells, in which it is accumulated in a denatured form, i.e. a conformational state without biological activity, various steps have to be taken to obtain the protein in its correctly refolded form. For example, bacterial cells carrying inclusion bodies are disintegrated, the inclusion bodies harvested by centrifugation and then dissolved in a buffer containing a chaotropic agent. The denatured protein is then transferred into an environment that favours the recovery of its native conformation. Before adopting its native state, the protein undergoes a transition through various semi-stable intermediates. Since intermediates have highly exposed hydrophobic domains, which are prone to associate, they tend to form aggregates. In principle, refolding may be considered as a race against aggregate formation, which usually follows second order reaction kinetics, while refolding of the protein follows first order reaction kinetics (Buchner, J. and Rudolph, R., *Current Opinion Biotechnology* 2:532–538 (1991)).

With the currently available methods, refolding of proteins is achieved by diluting the protein in a refolding buffer in a batch or continuous mode (Halenbeck, R., et al., *Bio/technology* 7:710–715 (1989); Kiefhaber, T., et al., *Biotechnology (NY)* 9:825–829 (1991); Lilie, H., et al., *Curr. Opin. Biotechnol.* 9:497–501 (1998); Clark, E. D., *Curr Opin Biotechnol.* 12:202–207 (2001); Yoshi, H., et al., *J. Chem. Eng. (Japan)* 34:211–215 (2001)). In these methods, batchwise dilution results in highly diluted protein solutions and therefore large process volumina, which often is the bottleneck in industrial processes.

In another approach the folding pathway is simulated in vivo by adding chaperons and/or minichaperons, and/or enzymes that catalyze certain steps in the folding pathway (Noiva, R., *Protein Expr Purif.* 5:1–13 (1994); Buchner, J., et al., *Biotechnology (N.Y.)* 10:682–685 (1992); Carlson, J. D. and Yarmush, M. L., *Biotechnology (N.Y.)* 10:86–91 (1992); Guise, A. D. and Chaudhuri, J. B., *Biotechnol. Prog.* 14:343–346 (1998); Kohler, R. J., et al., *Biotechnol. Prog.* 16:671–675 (2000); Shimizu, H., et al., *Biotechnol. Prog.* 16:248–253 (2000)). Complex refolding reactor systems comprising series of tanks have been designed to improve the refolding reaction (Katoh, S. and Katoh, Y., 2000 35:1119–1124 (2000)).

In another approach, the helper proteins and enzymes are immobilized to a solid phase. Then the protein solution is passed over a so-called Packed Bed containing the immobilized helper proteins and/or helper enzymes, thus being folded into its native conformation (Phadtare, S., et al., *Biochim Biophys Acta* 1208:189–192 (1994); Altamirano, M. M., et al., *Proc Natl. Acad. Sci. USA* 94:3576–3578 (1997); Altamirano, M. M., et al., *Nat Biotechnol,* 17:187–191 (1999); Preston, N. S., et al., *Biochim Biophys Acta* 1426:99–109 (1999)). Since the folding helper proteins and enzymes must be present in a stoichiometric ratio, this process requires almost the same amount of helper proteins, which in turn have to be produced by recombinant DNA technology, as the finally obtained product. In addition, to improve folding, the helper proteins are usually fused to the protein of interest, which requires further processing of the fusion protein. For these reasons, this strategy is very cost intensive.

Since a certain protein fraction is lost in the form of aggregates, refolding of the protein in free solution or in the matrix-assisted process is not efficient enough to transfer the denatured protein into the folded form in a quantitative way.

A protein can be refolded from its denatured conformation to the correctly folded conformation by transferring it into an environment that favors the change to the native conformation. During this rearrangement, the protein passes through several intermediate conformational states, which are prone to form aggregates. Depending on the individual protein and on the environmental conditions, the aggregates may precipitate. Independent of whether the aggregates remain soluble or whether they precipitate, this process leads to dramatic losses in the yield of correctly folded protein. In general, the folding of a protein to its native conformation follows first order reaction kinetics, while the formation of aggregates from intermediates follows second or higher order reaction kinetics.

It was an object of the invention to provide an efficient method for refolding a protein from a denatured state, which overcomes the shortcomings of the currently used methods and which can be operated without using helper proteins.

The solution of the problem underlying the invention is based on the consideration that the chromatographic separation process may be improved by running it continuously. In addition, it was hypothesized that recycling the intermediate forms of the protein may further allow both to improve the yield of a recombinant protein and to work at high protein concentrations, which would significantly reduce the process volume.

SUMMARY OF THE INVENTION

The present invention relates to a method for obtaining a biologically active recombinant protein by reconstituting the protein from a denatured state to its active form, wherein a feed solution containing the recombinant protein of interest in its denatured and/or in biologically inactive intermediate forms is subjected to a chromatographic separation process, in which the protein is reconstituted under conditions that promote refolding of the protein and the intermediate forms are separated from the refolded protein, characterized in that the denatured and/or in inactive intermediate forms are separated from the refolded final product in a continuous or quasi-continuouschromatographic method.

The term "denatured form", in the meaning of the present invention, designates the biologically inactive form of the expressed protein of interest, as obtained as a product of the recombinant production process, usually as obtained after dissolving the inclusion bodies.

The term "intermediate forms" or "intermediates" in the meaning of the present invention, designates the forms that the protein passes through between its denatured form and its reconstituted (refolded) native and biologically active state. The intermediates, which are biologically inactive or have a lower biological activity than the native protein, may be in the form of aggregates. (The term "inactive", in the context with intermediate forms, also encompasses forms of the protein with a lower activity as compared to the biologically fully active form of the protein.)

DETAILED DESCRIPTION OF THE INVENTION

Figure 1:
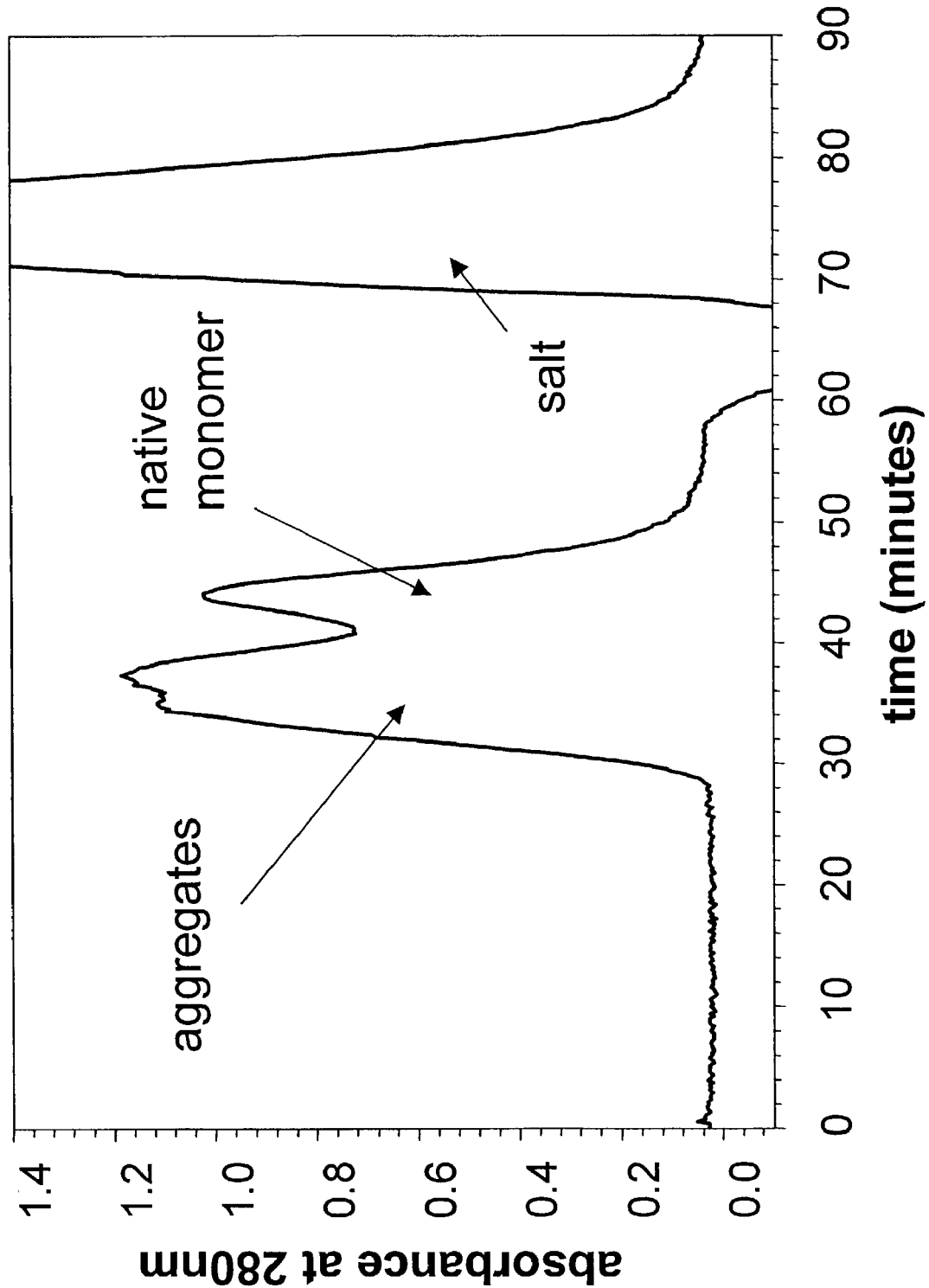
FIG. 1. Refolding of denatured and reduced α-lactalbumin by size exclusion chromatography on Superdex 75 PrepGrade column at a linear velocity of 30 cm/h.

In a preferred embodiment, the intermediate forms that have been separated form the refolded protein are reintroduced (recycled) into the feed solution and thus undergo the reconstitution process at least one additional time. The intermediates, when separated by the process of the invention, may still contain a fraction of denatured protein.

In order to keep the chromatography medium, usually a gel, properly working, it has to be regenerated. This is achieved by a regeneration solution that is applied to the packed bed. Depending on the chemical properties of the chromatography medium, this solution may be either a strong alkaline solution or a strong acidic solution, or a chaotropic buffer, or an organic solvent, e.g. ethanol, or an aqueous buffer supplemented with an organic solvent, or an aqueous buffer with an ionic or non-ionic detergent. The regenerating solution (regenerate) must be able to remove irreversibly bound protein fractions from the chromatography medium. The regenerate may be the feed solution itself or it may different from the feed solution and applied to the chromatographic medium separately from the feed solution.

In the case that the regenerate that exits the chromatographic process contains a significant amount ($\geq 10\%$) of intermediates, it is, in a preferred embodiment, recycled to the process, either separately or by combining it with the eluate stream that contains the intermediates.

In a particularly preferred embodiment, the eluate and/or regenerate containing the intermediate forms can be concentrated and/or diafiltrated before it is reintroduced into the starting feed solution. Thereby, yield and productivity of the refolding process is further improved. Concentration may be achieved by conventional means, e.g. by ultrafiltration (in the case of soluble intermediates) or microfiltration (in the case of insoluble intermediates/aggregates).

In the following, referring to the protein, the term "refolding" is used for "reconstituting from a denatured state to its active form".

The (starting) feed solution is the solution that has been obtained from fermentation of bacterial, yeast, fungal, plant or animal cells carrying an expression vector encoding a heterologous protein of interest.

In the present invention, the feed solution is usually obtained from conventional microbiological fermentation. The feed solution contains the recombinant protein in the solubilized form as obtained from the inclusion bodies.

The feed solution contains, besides buffer substances, components that promote the dissociation of the recycled aggregates, e.g. chaotropic agents such as urea, guanidinium chloride (GuHCl), sodium and/or potassium thiocyanate, and reducing agents such as mercaptoethanol, dithiothreitol, monothioglycerol. Typical compositions and conditions are known in the art, they have been extensively described in the literature (Lilie, H., et al., *Curr. Opin. Biotechnol.* 9:497–501 (1998); Clark, E. D., *Curr Opin Biotechnol.* 12:202–207 (2001); Clark, E. D., et al., *Methods Enzymol.* 309:217–236 (1999)). In the case of size exclusion chromatography, a feed solution containing denaturating and/or reducing agents, may, at the same time, serve as a regenerating solution.

Starting from a given feed solution, the person skilled in the art is familiar with the measures that have to be taken to provide the conditions that promote refolding, i.e. appropriate refolding environment, during the chromatographic process of the invention. First, to obtain conditions that promote refolding of the protein, the chaotropic and/or reducing agents required for solubilization of the inclusion bodies and denaturation of the protein that are contained in the feed solution have to be removed, either completely or to an extent that is tolerated by the protein. In the present invention, this is achieved during the chromatographic process by washing out the above-mentioned agents with a suitable refolding buffer, e.g. a Tris or phosphate buffer, such that an optimal refolding environment in terms of pH, conductivity and temperature is given (Lilie, H., et al., *Curr. Opin. Biotechnol.* 9:497–501 (1998); Clark, E. D., *Curr Opin Biotechnol.* 12:202–207 (2001); Clark, E. D., et al., *Methods Enzymol.* 309:217–236 (1999)).

The feed solution may be diluted to achieve partial refolding of the protein before it undergoes the chromatographic refolding process.

To ensure the optimal conditions for refolding, the refolding buffer may be supplemented by agents that provide the optimal redox potential and thus promote the correct formation of disulfide bridges, e.g. oxidized and reduced glutathione or cystine/cysteine, and/or agents that prevent aggregation, e.g. L-arginine, urea, polyethyleneglycol (Lilie, H., et al., *Curr. Opin. Biotechnol.* 9:497–501 (1998); Clark, E. D., *Curr Opin Biotechnol.* 12:202–207 (2001); Clark, E. D., et al., *Methods Enzymol.* 309:217–236 (1999)).

The separation of the intermediates from the correctly folded protein can be accomplished by any continuous or quasi-continuous chromatographic method that has been proven useful for the separation of proteins.

A great number of standard chromatographic methods that are routinely used for protein separation are known from the literature, most of them being applicable on commercially available devices, e.g. chromatographic columns. Depending on the principle of separation, the methods are divided into ion-exchange chromatography, affinity chromatography, hydrophobic interaction chromatography, reversed phase chromatography, covalent chromatography, size exclusion chromatography or adsorption chromatography.

In principle, these chromatographic methods can be conducted in a batchwise, a quasi-continuous or a continuous mode of operation. In the batchwise mode of operation, the feed solution is loaded onto a chromatographic support, e.g. a packed bed or an expanded bed, and the protein, depending on its affinity to the stationary phase, is either strongly retained or passes through the column. In the case the protein is strongly retained, it can be desorbed by a change of running conditions after the unbound material has been washed out.

The batch process can be transferred to a quasi-continuous mode either by working with several columns in a sequential manner or by placing the columns in a manifold of valves to allow a continuous operation, termed "carousel chromatography".

Any chromatographic protein separation method, provided it can be conducted in a quasi-continuous or continuous mode, can be used in the present invention. The person skilled in the art is familiar with these methods and can select the most appropriate one to a given separation requirement.

Annular chromatography (AC), carrousel chromatography, simulated moving bed (SMB) and true moving bed (TMB) chromatography are the most widely used chromatographic separation systems that are operated in a continuous or quasi-continuous manner. The advantages of AC over SMB and TMB lie in the application of a gradient elution and the separation of multi-component mixtures (Heuer, C., et al., *Chemie Ingenieur Technik* 69:1535–1546 (1997)).

In a preferred embodiment, the method of the invention is annular chromatography. This method has been suggested for a great variety of separation problems ranging from small molecules to biopolymer separations (Begovich, J. M., et al., *Sep. Sci. Tech.* 18:1167–1191 (1983); Begovich, J. M. and Sisson, W. G., *AIChE Journal* 30:705–710 (1984); Bloomingburg, G. F., et al., *Ind. Eng. Chem. Res.* 30:1061–1067 (1991); Bloomingburg, G. F. and Carta, G., *Chem. Eng. J.* 55:B19-B27 (1994); Buchacher, A., et al., *Biotechnology Progress* 17:140–149 (2000); Byers, C. H., et al., *Appl.Biochem.Biotechnol.* 20–21:635–654 (1989); Byers, C. H., et al., *Biotechnol. Prog.* 6:13–20 (1990); Canon, R. M., et al., *Separation Science and Technology* 15:655–678 (1980); Canon, R. M. and Sisson, W. G., *J. Liqu. Chrom.* 1:427–441 (1978); Carta, G., et al., *Chem. Eng. Com.* 79:207–227 (1989); Carta, G. and Byers, C. H., "Novel Applications of Continuous Annular Chromatography," in *New Directions in Sorption Technology,* Keller, G. E. and Yang, R. T., eds., Butterworth (1989); Dalvie, S. K., et al., "Mathematical model of a rotating annular continuous size exclusion chromatography, in *Downstream Processing and Bioseparation,* Hamel, J.-F. P., et al., eds. (1990), pp. 268–284; Reissner, K., et al., *J. Chromatogr.* 763:49–56 (1997); Scott, C. D., et al., *J. Chromatogr.* 126:381–400 (1976); Uretschläger, A., et al., *J. Chrom. A* 908:243–250 (2001); Wolfgang, J., et al., *Sep. Sci. Tech.* 32:71–82 (1997); Yamanishi, Y. and Yonemoto, T., *In. Eng. Chem. Res.* 36:3809–3814 (1997); Tagahashi, Y. and Goto, S., *Sep. Sci. Techn.,* 29:1311–1318 (1994); Takahashi, Y. and Goto, S., *J. Chem. Eng.* 24:121–123 (1991); Takahashi, Y. and Goto, S., *Sep. Sci. Tech.* 26:1–13 (1991); Takahashi, Y. and Goto, S., *J. Chem. Eng.* 24:460–465 (1991); Takahashi, Y. and Goto, *J. Chem. Eng.* 25:403–407 (1992); Takahashi, Y. and Goto, S., *Sep. Sci. Techn.* 29:1311–1318 (1994); Sisson, W. G., et al., *CHEMTECH* 18:498–501 (1988); Sisson, W. G., et al., *Prep. Chrom.* 1:139–162 (1989); Goto, M. and Goto, S., *J. Chem. Eng.* 20:598–603 (1987); Kitakawa, A., et al., *Sep. Sci. Tech.* 30:3089–3110 (1995)). The original concept of an annular chromatograph, as proposed by Martin (Martin, A. V. P., *Faraday Soc.* 7:332–336 (1949)) and realized by Fox et al. (Fox, J. B., et al., *J. Chromatogr. A* 43:48–54 (1969); Fox, J. B. and Nicholas, R. A., *J. Chromatogr. A* 43:61–65 (1969); Fox, J. B., *J. Chromatogr. A* 43:55–60 (1969)), was further developed at the Oak Ridge National Laboratory to operate the system under a certain pressure (Begovich, J. M., et al., *Sep. Sci. Tech.* 18:1167–1191 (1983); Scott, C. D., et al., *J. Chromatogr.* 126:381–400 (1976); Sisson, W. G., et al., *Prep. Chrom.* 1:139–162 (1989)). The Pressurized-Continuous Annular Chromatograph (P-CAC) was designed as a closed system. Two concentric cylinders form an annulus, into which the chromatography medium is packed. Feed and eluent (which is, in the method of the invention, the refolding buffer) are introduced in a continuous way at the top of the bed. The entire bed slowly rotates, while the feed solution is introduced from a stationary entry and the eluent is uniformly present everywhere else around the annulus. The separation of the feed solution into single components is caused by the rotation of the sorbent. The separated components appear as helical bands, each of which has a characteristic, stationary exit point. Three factors have an effect on the location of the exit point: (a) eluent velocity, (b) rotation rate of the annulus, and (c) the distribution coefficient.

Any annular chromatographic method and device can be used in the present invention. Examples of annular chromatographs that are suitable for use in the present invention are described in the literature (see the previous paragraph) and in the following patent applications:

WO 98/45699, WO 99/28740, WO 01/388866, EP 1 134 581. The devices can be obtained commercially, e.g. from Prior, Götzis, Austria.

In the case of using annular chromatography in the method of the invention, the annulus is packed with a special chromatography medium allowing separation according to either ion-exchange chromatography, affinity chromatography, hydrophobic interaction chromatography, reversed phase chromatography, covalent chromatography, size exclusion chromatography or adsorption chromatography. The choice of chromatographic principle depends on structure of the protein, the concentration of the protein, the amount and nature of the contaminants, the overall process flow scheme and the availability of a particular protein ligand (in the latter case, the method of choice usually is affinity chromatography).

The feed solution containing the denatured protein (and optionally spontaneously formed intermediates and aggregates) is continuously fed to the rotating annulus that is packed with the chromatography medium. The medium, usually a gel, is perfused with a buffer promoting refolding of the protein (the refolding buffer, as described above). While the proteins pass through the column, the refolding process takes place. Due to their physicochemical properties (such as molecular size, hydrophobicity, accessible charged and hydrophobic groups, solubility etc.) of the intermediates, the native refolded protein and the intermediates are retained differently. According to their different retention properties, the different states of the protein, i.e. the intermediates and the biologically active protein, respectively, elute at different exit points of the annulus. In a preferred embodiment, the exit stream containing the intermediates, possibly in the form of soluble or suspended aggregates, is collected and recycled to the feed solution. To increase the amount of intermediates/aggregates, they can be concentrated by any suitable concentration device, e.g. a tangential flow ultrafiltration unit. The optionally concentrated, recycled intermediates/aggregates become then components of the feed solution and undergo at least one additional refolding process.

In an alternative embodiment that uses annular chromatography, the denatured protein is adsorbed and completely or partially refolds during the adsorption process, which occurs in the presence of refolding buffer. The conditions for subsequent desorption must also favour refolding, i.e. they have to ensure, on the one hand, that the protein that has already refolded during adsorption maintains its native conformation and, on the other hand, that refolding of the remaining protein is promoted. The protein fractions, which have not refolded, can be separated from the refolded protein during the adsorption and/or desorption step and are, in a preferred embodiment, recycled by adding them to the feed solution.

The annular chromatography process results in a stoichiometric conversion of the denatured protein to its correctly folded native state. Another advantage is a decrease in process volume and the possibility to maintain a continuous process. In order to keep the chromatography gel properly working, it has to be regenerated. A regeneration solution is applied to the packed bed at a position distant enough from the feed inlet position to avoid mixing of the regeneration solution with the feed solution. The composition of the regenerating solution depends on the chemical properties of the chromatographygel, as described above. The regenerate eluates at a position different from the eluate containing the intermediates and the native, refolded protein. The regenerate can be, in case that it contains significant concentrations of protein, recycled. This may be done by re-introducing it into the starting feed solution by itself or by combining it with the eluate containing the intermediates.

In another preferred embodiment, the chromatographic method used in the method of the invention is the Simulated Moving Bed (SMB) process, which was first developed in the early sixties by the Universal Oil Product Company (Broughton, D. B., *Sep. Sci. Technol.* 19:723–736 (1984); Schulte, M. and Strube, J., *J. Chromatogr. A* 906:399–416 (2001)). It was mainly applied to industrial scale separations, such as the separation of xylenes or the separation of fructose and glucose. By employing a suitable system of adsorbant and eluate, a feed stream is separated into two withdrawal streams containing the pure components of a binary or pseudo-binary mixture (a mixture of two or more compounds that, due to their different physico-chemical properties, can be divided into two fractions). The SMB process divides a large column into a finite number of small sections, also termed "zones", between which withdrawal tubes are situated. These tubes are connected with the inlets and outlets in a cyclic mode via a specially designed rotary valve. Switching the rotary valve at a defined point of time simulates a countercurrent flow of solid and fluid phase. Hidajat et al. (Hidajat, K., et al., *Chem. Eng. Sci.* 41:2953–2956 (1986)) have shown that the SMB is equivalent to TMB. For SMB applications one large column may be used or the large column may be substituted by a number of smaller columns. There are inlets or outlets for the feed solution, the eluent buffer, extract and raffinate, called nodes, dividing the arrangements of columns into four zones. Special valves allow the liquid to flow in only one direction. The inlets and outlets are arranged in a predefined manner. These nodes are switched in the same direction as the fluid flows or the columns are switched counterwise to this direction at a defined time interval. As a result, there is a countercurrent flow of solid and fluid phase.

In the SMB mode, the method of the invention is operated in the quasi-continuous mode and preferably carried out as follows:

At time $t_0$ the feed solution containing the denatured protein (and optionally intermediates) is continuously injected between zones II and III. The zones are defined analogously to the true moving bed; at zone I the liquid is introduced, between zone I and II the extract is collected, between zone II and III the feed solution is introduced, between zone III and IV the raffinate is collected. Hereby component A (the aggregates) is defined as the least adsorbable fraction, and component B (the refolded protein including the intermediates and additional contaminating proteins) as the more strongly retained component. The feed solution is pushed into zone III by the eluent (refolding buffer). Component A (least adsorbable) migrates faster than component B (strongly adsorbed or retained). Before component A reaches zone IV, a part of the protein solution is withdrawn by the raffinate outlet. The remaining part is transported into zone IV. Just before the front of component B reaches the raffinate outlet, the inlets and outlets have to be switched to the next position to avoid a contamination of raffinate. The switching has to be in the same direction as the liquid flow, while the column remains stationary in space. The saturated columns in zone II are cleaned by fresh eluent. The mixture flowing out from zone II is mixed with the feed solution and transported into zone III. In this section, component A is displaced by component B. The faster migrating component A reaches the raffinate outlet again. Before the breakthrough of the component B at the raffinate outlet point, there is a switching into the $3^{rd}$ state. A full cycle is completed after the fourth switching, assuming the simplest configuration of a SMB or TMB.

There is an apparent rotation of the columns of 360°. The cyclic steady state of the system is reached after several full cycles. At the extract and raffinate outlet, the desorption and the breakthrough fronts of the components A and B can be collected. The intermediates (component B) are continuously recycled to the feed solution.

In a continuous mode of operation the protein concentration of the eluate stream is constant over time, e.g. in annular chromatography at a given exit. In contrast, in the quasi-continuous mode it changes cyclically over time, e.g. in SMB due to the distinct zones.

In its extreme form, a continuous separation process is divided into an indefinite number of separation sections.

As to the refolding environment during the chromatographic process, for many industrially useful proteins guidance for defining the parameters that promote refolding are available in the literature (Lilie, H., et al., *Curr. Opin. Biotechnol.* 9:497–501 (1998); Clark, E. D., *Curr Opin Biotechnol.* 12:202–207 (2001); Clark, E. D., et al., *Methods Enzymol.* 309:217–236 (1999)). For a novel protein of interest, depending on the specific protein, given a feed solution from a fermentation process, the refolding parameters can be determined and optimized in serial experiments by performing dilution experiments in a small-scale batch mode. These experiments can be conducted by varying the refolding buffer with regard to the above listed factors, e.g. pH, redox potential, etc. The obtained conditions are transferred on a chromatography column. The elution positions for the various protein forms, i.e. the refolded, intermediate and aggregate forms, are determined. The suitable chromatographic process is then designed on the basis of these values.

Similarly to the composition of the refolding buffer, the other chromatographic process parameters, e.g. feed flow rate, eluent flow rate, feed concentration, column length and diameter, temperature etc. can be determined and optimized depending on the individual protein. A prerequisite for the separation is that it has a different selectivity for the aggregates, the intermediates and the refolded form of the protein. The aggregated forms and the intermediates differ from the native molecule at least in size, hydrophobicity and charge.

For the preferred embodiment of the invention, in which the eluent containing intermediates is recycled, the re-circulation (recycling) ratio is adjusted depending on the mode of chromatographic separation. For adsorptive separation methods such as ion exchange chromatography and adsorption chromatography, the feed solution can be diluted to any extent with the solution containing the recycled aggregates. The re-circulation (recycling) ratio depends on the eluate stream containing the intermediates/aggregates. In size exclusion methods, the volume of recycled feed is critical, because in these methods the separation is strongly effected by the feed volume and flow rate of the eluent. In these methods, care needs to be taken that the amount of feed solution should never exceed one third of the total column volume. For critical separation problems, this amount is even lower. Thus a concentration step has to be inserted after collection of the eluted intermediates/aggregates. This can be achieved by a conventional ultrafiltration system.

In another preferred embodiment, the method of the invention is carrousel chromatography. Suitable devices are commercially available, e.g. from SepTor Technologies BV, Utrecht. The Septor is a carrousel type quasi-continuous system. In order to transport the chromatography columns through all steps in the process cycle, they are mounted on a slowly rotating carousel. The carrousel typically rotates clockwise and includes all process steps as applied in a conventional chromatography step (equilibration, loading of the feed solution, washing, elution, regeneration). In order for the columns to move along all different sections in the process cycle, the columns are connected to a multiport indexing valve. The stream of the eluate containing the intermediates/aggregates is preferably recycled to the feed stream. Prior to recycling, the eluate solution is preferably concentrated.

Figure 10:
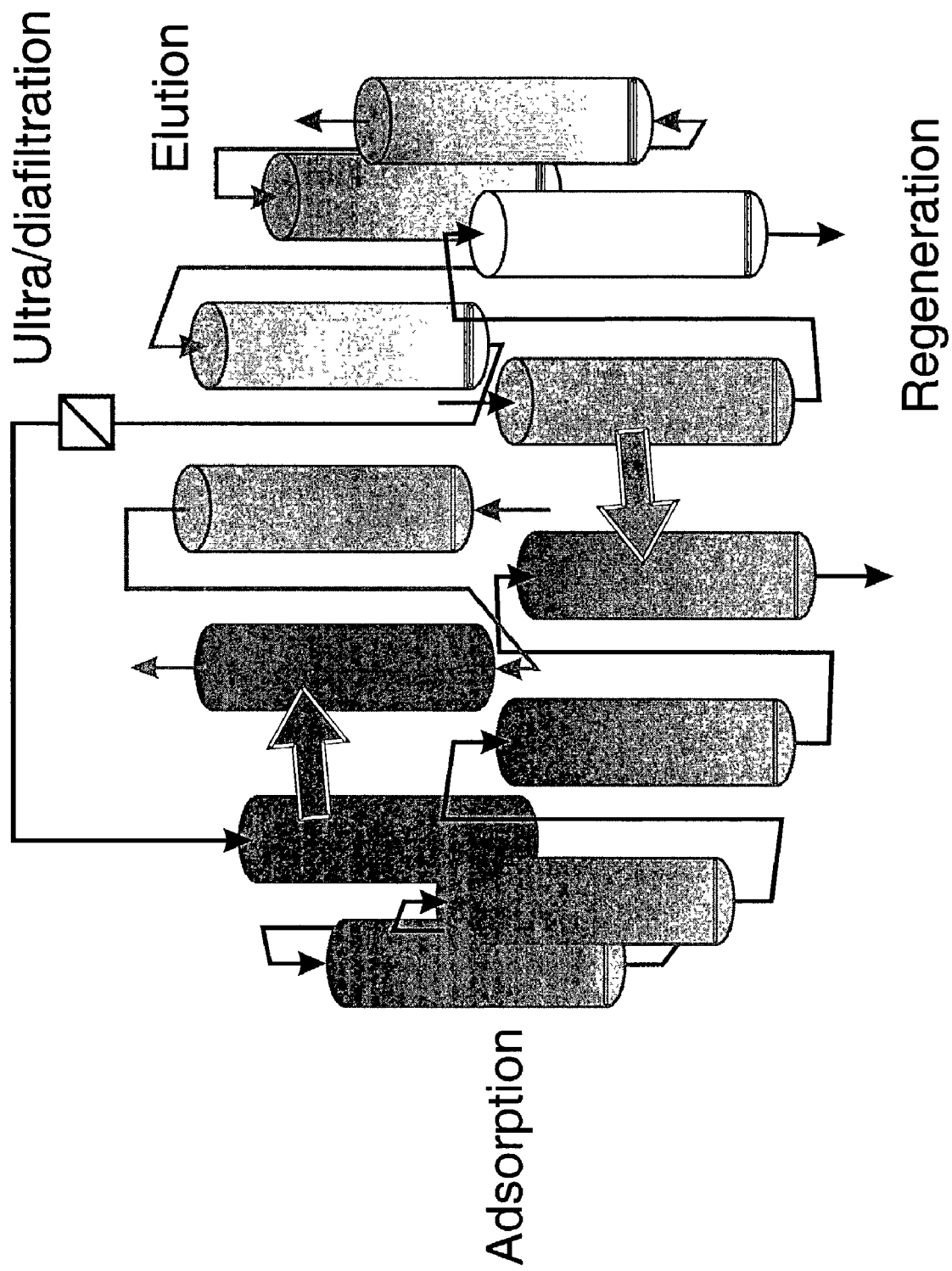

FIG. 10 shows a typical scheme of caroussel chromatography.

Overall, the method of the invention has the following advantages: it allows for high protein concentrations in the feed solution, it is highly efficient in terms of refolding yield, it allows for separation of the refolded protein from the intermediates and it can be operated without employing chaperons. (However, the method of the invention does not exclude the use of chaperons, which may be immobilized on the chromatographic column, which thus operates as a catalytic refolding reactor, or which may applied as components of the refolding buffer).

The method of the invention can be operated from small laboratory scale to industrial scale. The chromatographic devices used in the method of the invention are commercially available and can be, in terms of size and performance, supplied from the manufacturers according to the customer's needs; for recombinant proteins, the required capacities usually range from a few mg to kg amounts.

EXAMPLES

Example 1

Continuous Refolding of α-lactalbumin by Matrix-assisted Refolding on Gel-permeation Chromatography a) Before transferring the process into a continuous mode, refolding was tested on a conventional packed bed using a Superdex 75 PrepGrade column from AP biotech (Uppsala, Sweden). α-lactalbumin was dissolved in a 50 mM tris buffer, pH 8.5 supplemented with 6 M GuHCl and 20 mM dithiothreitol. These conditions induce complete denaturation of protein and splitting of the disulphide bridges into free sulfhydryl groups. The protein concentration was 3.7 mg/ml. A Superdex 75 PrepGrade column with 1.6 cm i.d. and 37 cm height was packed and 1 ml feed (reduced α-lactalbumin) was injected after the column had been equilibrated with a 50 mM Tris buffer supplemented with 2 mM cysteine, 2 mM cystine and 10 mM $CaCl_2$ at a flow rate of 30 cm/h. While passing through the column, the refolded proteins were separated from the aggregates (FIG. 1). The column effluent was continuously monitored at 280 nm. The native protein and the aggregates were analyzed by analytical size exclusion chromatography and RP-HPLC. The refolding yield was about 26 percent. The addition of 0.25M L-Arginine into the refolding-buffer increased the yield to 40%.

b) For the continuous refolding experiments, the same protein solutions and buffers were used. The Superdex 75 PrepGrade chromatography medium was packed onto a annular chromatography System, PCAC from Prior Separation Technology (Götzis, Austria). The PCAC consists of two concentric cylinders forming an annulus into which the stationary phase is packed. The outer cylinder had a diameter of 15 cm and the inner one a diameter of 14 cm, resulting in an annulus width of 0.5 cm. The upper part of the outer cylinder is made of glass and the lower part of polypropylene. The inner cylinder is made of polypropylene and is shorter than the outer one, leaving a head space at the top. Both cylinders are closed by a head from PEEK (Polyetheretherketone) through which the eluent and feed streams are inserted. The feed stream was pumped at the top of the gel bed through a fixed feed nozzle, whose tip was located within the layer of the glass beads. At the bottom of the unit, the two cylinders are attached to a stainless steel plate which contains 90 exit holes covered by a nylon filter (11 μm pore size). The bottom of the rotating column is connected to a fixed teflone slip-ring which also contains 90 exit ports connected to a short section of Tygon tubing (Norton Performance Plastic Corporation, Akron, Ohio, USA). The exit ports are evenly distributed at 4° intervals along the annulus. The column was packed to a height of 41 cm cm with Superdex 75 PrepGrade. The bed of the glass beads was 2.6 cm high.

The system was additionally equipped with a pump for recycling the aggregates to the feed solution. The transfer of a batchwise separation into a continuous one is made by transformation of the elution time (t) and angular velocity (ω) into angular displacement (θ).

$$\theta = \omega * t$$

From this calculation, the exit point of the various separated components can be determined.

Figure 2:
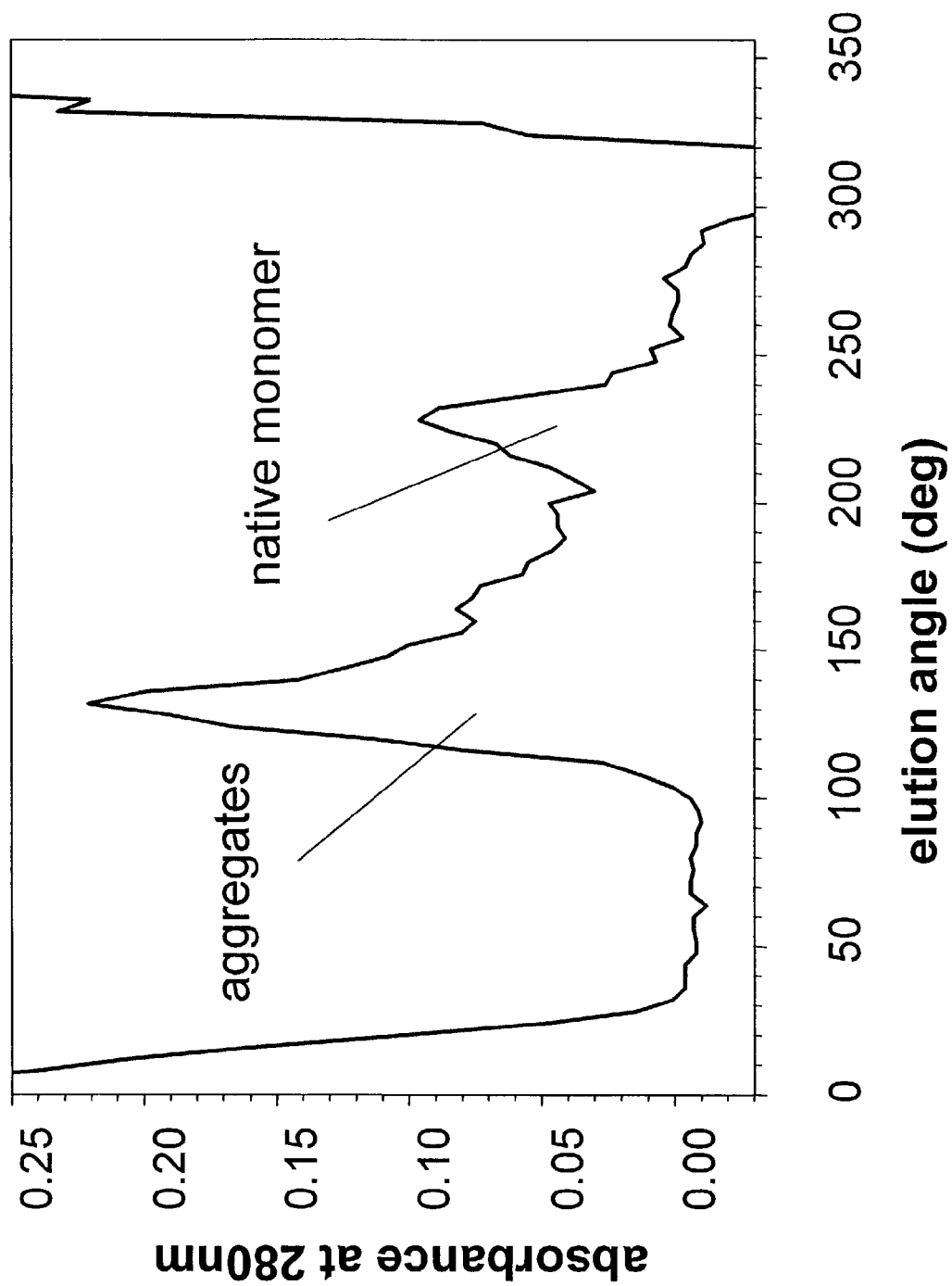
FIG. 2. Continuous refolding of denatured α-lactalbumin by annular size exclusion chromatography on Superdex 75 PrepGrade column at 250°/h and 30 cm/h.

Next, the refolding process was performed continuously. A rotation rate of 250°/h was applied and the eluent flow rate was 30 cm/h. A feed flow rate of 0.31 ml/min was applied. The chromatogram obtained after continuous refolding of lactalbumin by size exclusion chromatography is shown in FIG. 2.

After separation had reached a steady state, collection of the fractions containing the aggregates was started. Continuous concentration commenced when 50 ml were collected. Samples were drawn and the amount of aggregated protein and native protein was determined.

Figure 3:
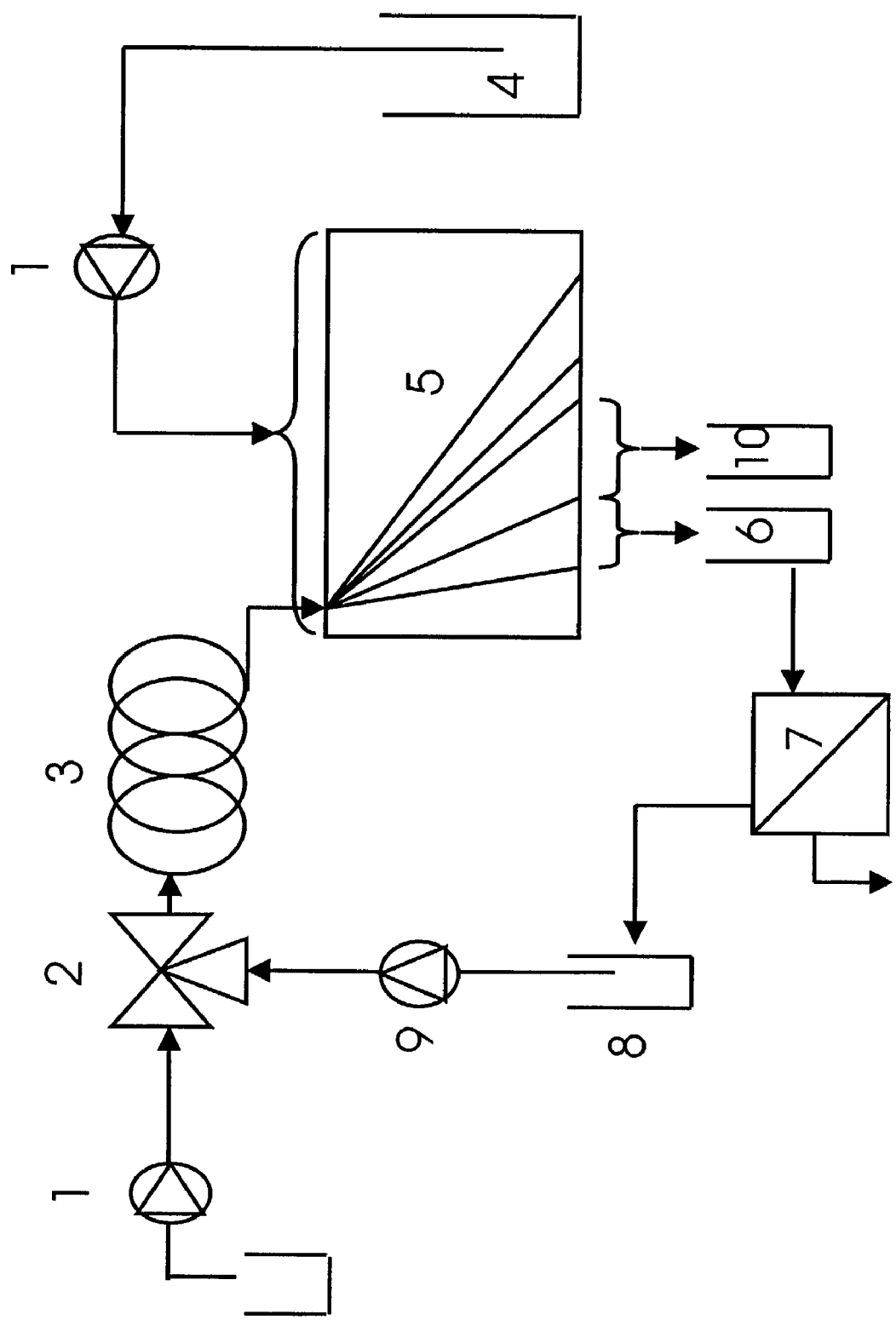
FIG. 3. Schematic drawing of experimental setup for continuous refolding by annular chromatography and recycling of aggregates FIG. 4A. Reversed phase HPLC chromatogram of fractions from matrix assisted refolding with HIC FIG. 4B. Reversed phase HPLC chromatogram of native α-lactalbumin FIG. 4C. Reversed phase HPLC chromatogram of denatured and reduced α-lactalbumin FIG. 5. Matrix assisted refolding of rHuAFP on Sephacryl 200HR FIG. 6. Capture step of refolded rHuAFP on Q-Sepharose XL FIG. 7. SDS-PAGE (silver stain) of native protein fraction eluted from Q-Sepharose XL FIG. 8. Analytical size exclusion chromatography of native protein fraction eluted from Q-Sepharose XL FIG. 9. Continuous refolding of denatured and reduced α-lactalbumin by annular ion exchange chromatography FIG. 10. Schematic illustration of caroussel chromatography

The effluent of those ports where the aggregates are eluted was collected continuously and concentrated by tangential flow filtration using a Millipore tangential flow filtration system with Biomax 5K membranes. The concentration was adjusted to approx. 1 mg/ml. A schematic drawing of the experimental setup for continuous refolding by annular chromatography and recycling of aggregates is shown in FIG. 3: 1 is the feed pump delivering the reduced lactalbumin, 2 is the mixer for blending of fresh feed with recycled feed after concentration by tangential flow filtration. 3 is the reaction loop to complete reduction of recycled aggregates; 4 is the eluent pump for the annular chromatography system, 5 is the annular chromatography system, 6 a collecting device consisting of a simple glass bottle, 7 a tangential flow filtration device, 8 a vessel for collection of concentrated aggregates, 9 is the recycling pump and 10 a vessel for collection of refolded protein.

After the system had reached equilibrium, the refolding efficiency at a protein concentration of 3.7 mg/ml was raised from 26% without recycling to >80% with recycling.

Example 2

Continuous Refolding of Human Alpha-fetoprotein (rHuAFP) with the Annular Chromatography System PCAC and Estradiol Sepharose Human alpha-fetoprotein was expressed in *Escherichia coli* as described by Boismenu et al. (Bosmenu, R., et al., *Protein Expr. Purif.* 10:10–26 (1997)). The cells were expanded in 10×5 L shake flasks and harvested by a bucket centrifuge The resuspended cells were disintegrated by a high pressure homogenizer at 500 bar. The homogenate was clarified by centrifugation at 10.000 g and the sediment containing the inclusion bodies was dissolved in 6M urea by excessive stirring. This solution was partially refolded by dilution. The partially refolded solution was further processed by a continuous adsorption/desorption on estradiol sepharose. The estradiol sepharose was prepared as described by Feng et al. (Feng, W., et al., *J. Chromatogr. A* 852:161–173 (1999)) and packed into the annular chromatograph. The same annular chromatograph as in Example 1 was used. The refolded rHuAFP was bound to the estradiol sepharose and could be eluted in a concentrated form, while the non-refolded part was found in the flow through and recycled to the feed solution. In order to avoid excessive dilution of the feed, the recycled solution was concentrated by tangential flow filtration and urea was added to supplement for chaotropic activity in the feed solution.

Example 3

Continuous Refolding of α-lactalbumin on Hydrophobic Interaction Chromatography (HIC) Sorbents Bovine α-lactalbumin was dissolved in 50 mM Tris/HCl, 10 mM $CaCl_2$, pH 7.0, and denatured with 6 M GuHCl and 250 mM β-mercaptoethanol. This was performed at a concentration of 5 mg/ml at room temperature. The refolding took place at the HIC sorbent. As an example Macroprep Methyl from BioRad (Hercules, Calif., USA) was chosen. Prior to the loading of the denatured lactalbumin the column had been equilibrated with 1.5 M ammonium sulfate. The ammonium sulfate was dissolved in a 50 mM Tris/HCl, 10 mM $CaCl_2$, 2 mM cysteine/cystine buffer pH 7.0. Solid ammonium sulfate was added to the denatured protein solution to reach a final concentration of 1.5. M. Then 2.5 ml of the denaturated protein solution supplemented with ammonium sulfate was loaded on a 14 cm×1.0 cm i.d. methyl Sepharose column at a linear velocity of 100 cm/h. The column effluent was monitored at 280 nm. A residence time of 25 min of protein was sufficient to elute refolded protein with a 50 mM Tris/HCl, 10 mM $CaCl_2$, 2 mM cysteine/cystine buffer pH 7.0. The column was regenerated with 20% ethanol dissolved in water. This peak contained residual α-lactalbumin in the unfolded state.

Refolding was examined by reversed phase HPLC (Vydac C4,214TP54). Fully denatured α-LA was separated from oxidative folding intermediates and native protein by linear gradient elution from 37% to 45% acetonitril/water containing 0.1% TFA in 15 minutes at 1 ml/min and 30° C.

Figure 4A:
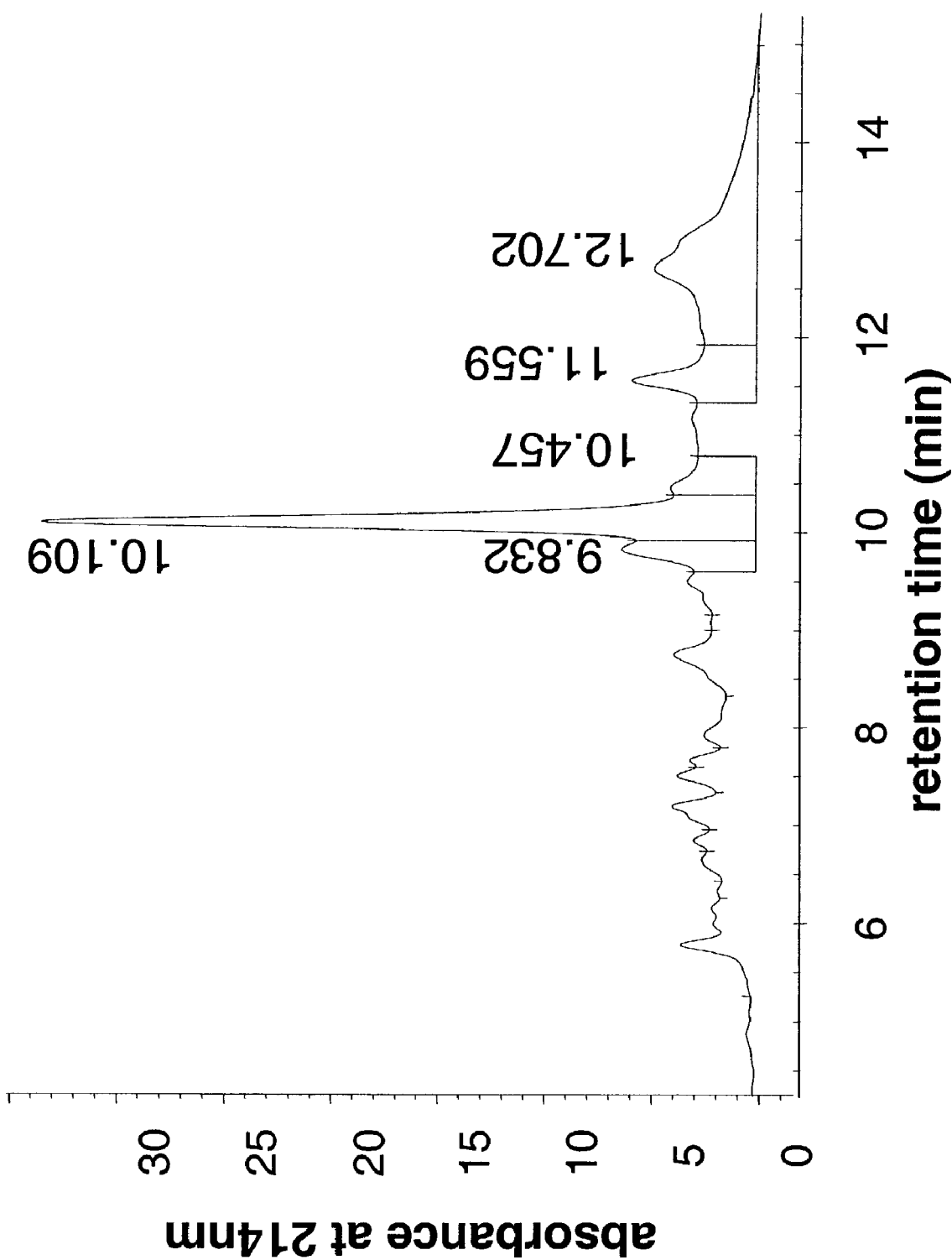
Figure 4B:
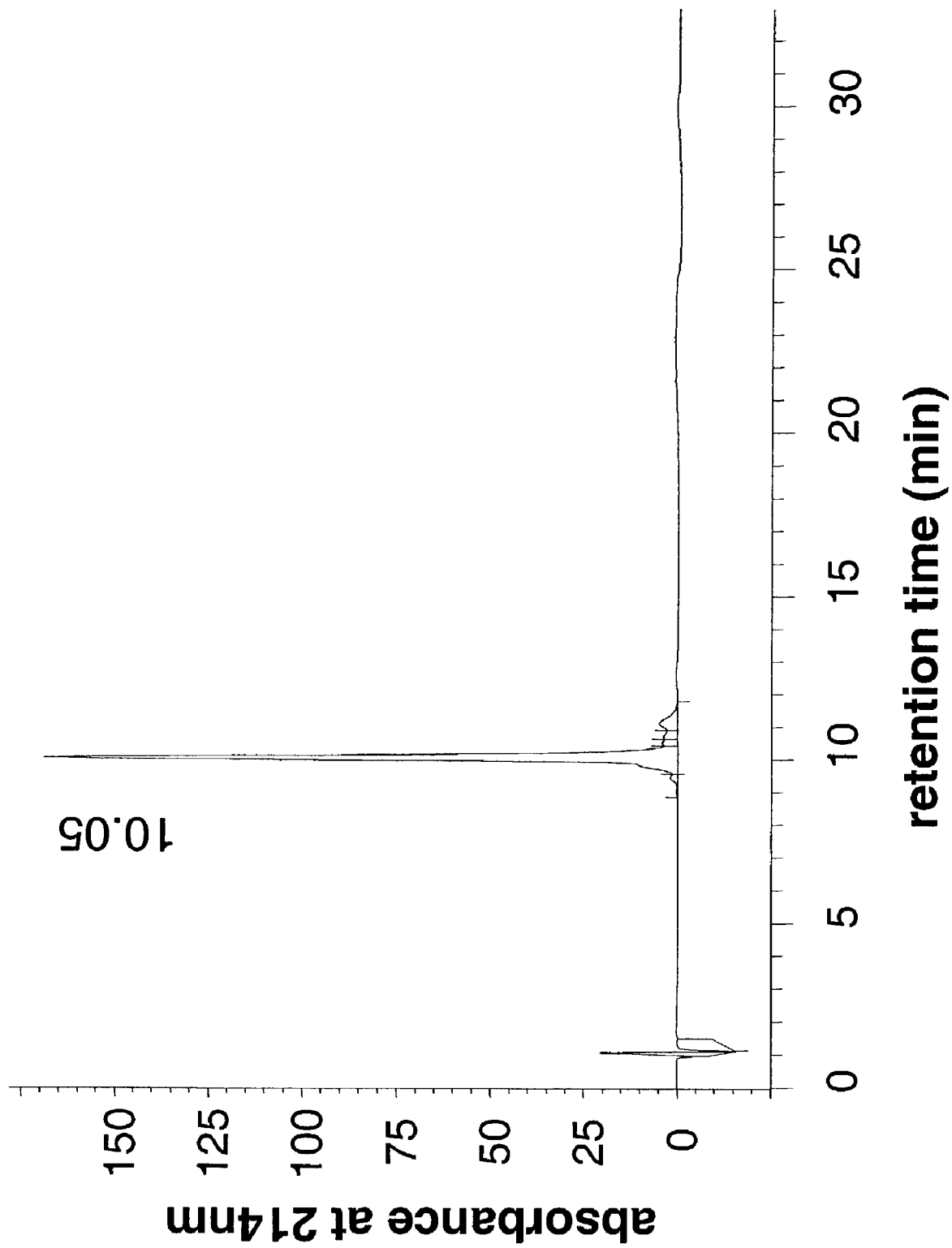
Figure 4C:
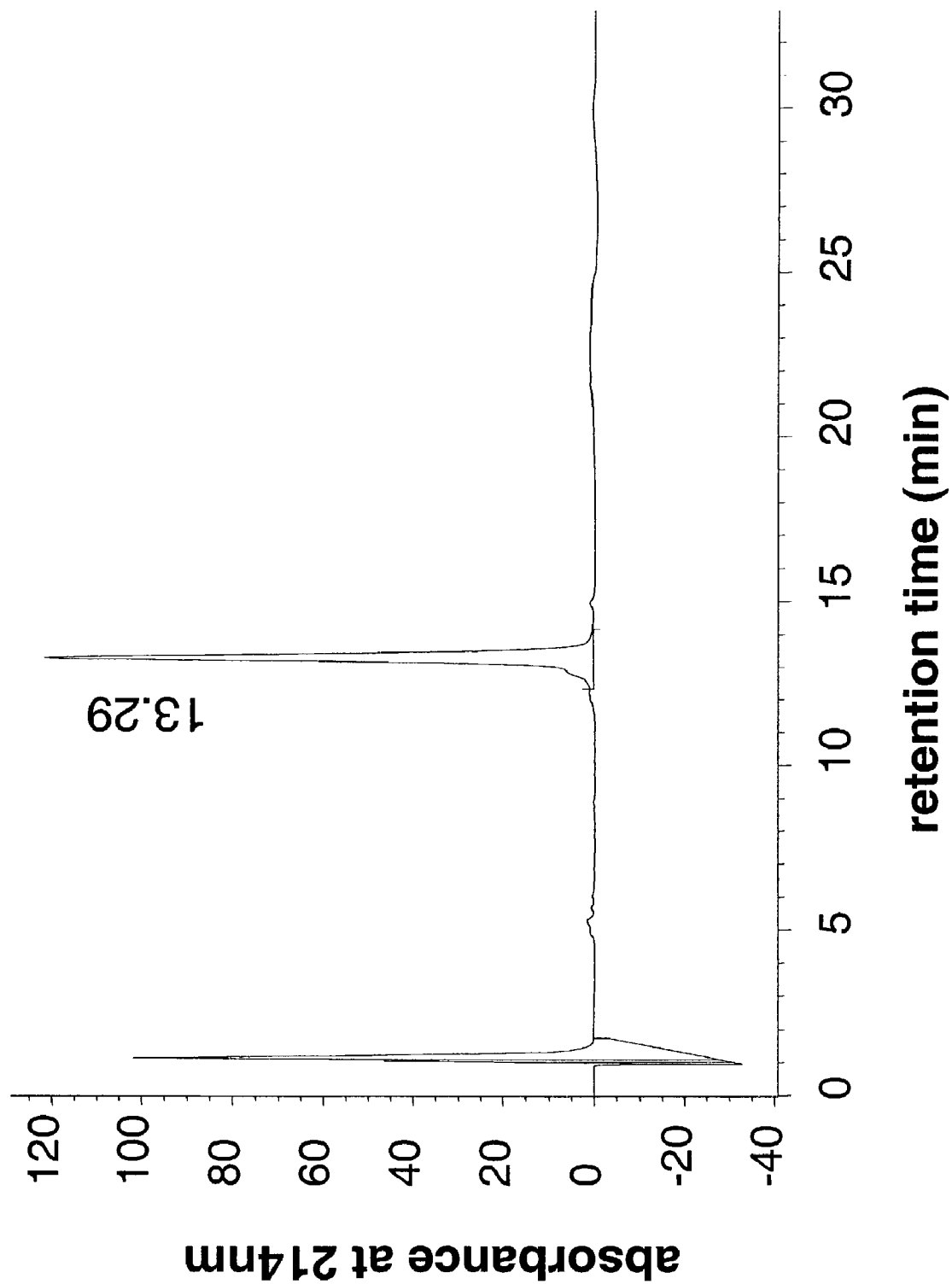

All runs were performed on an Agilent LC 1100 system. A Reversed phase HPLC chromatogram of fractions containing refolded protein after matrix assisted refolding with HIC is shown in FIG. 4A. RP-HPLC chromatograms of native and denatured/reduced α-lactalbumin are shown in FIGS. 4B and 4C, respectively.

These refolding conditions were transferred to continuous annular chromatography. Macroprep Methyl medium was packed into a annular chromatograph from Prior Separations Technologies (Götzis Austria). The system is described in Example 1. A column height of 14 cm was chosen and the annulus width was 0.5 cm. At positions 0–12° the denatured α-lactalbumin was introduced. At position 200° the lactalbumin was eluted with 50 mM Tris/HCl, 10 mM $CaCl_2$, 2 mM cysteine/cystine buffer pH 7.0 at position 300° the column was regenerated with 20% ethanol dissolved in water. The regenerate was continuously ultra-diafiltrated by a Millipore system using a Biomax 5 filter. As diafiltration buffer a 50 mM Tris/HCl, 10 mM $CaCl_2$, pH 7.0 in 6 M GuHCl, 250 mM β-mercaptoethanol and 1.5 M ammonium sulfate was used. The ultra-diafiltrated solution was recycled to the feed and the continuous refolding was performed until steady state conditions were reached.

Example 4

Continuous Refolding and Separation of Native Recombinant Human Alpha-Fetoprotein (rHuAFP), Folding Intermediates and Aggregates rHuAFP is a complex protein, which contains 16 disulfide bridges. It is produced in *E. coli* as inclusion body.

a) Before transferring the process to a combined continuous mode, the refolding and capture step of rHuAFP were tested on conventional chromatography columns packed with Sephacryl 200HR and Q-Sepharose XL from AP biotech (Uppsala, Sweden).

The inclusion bodies containing rHuAFP were isolated as described in example 1 and dissolved in 50 mM Tris-HCl, pH 8.5, 6M GuHCl and 100 mM DTT. The final rHuAFP concentration was about 0.5 mg/ml, the total protein concentration including protein impurities from host cells was approx. 5 mg/ml.

Figure 5:
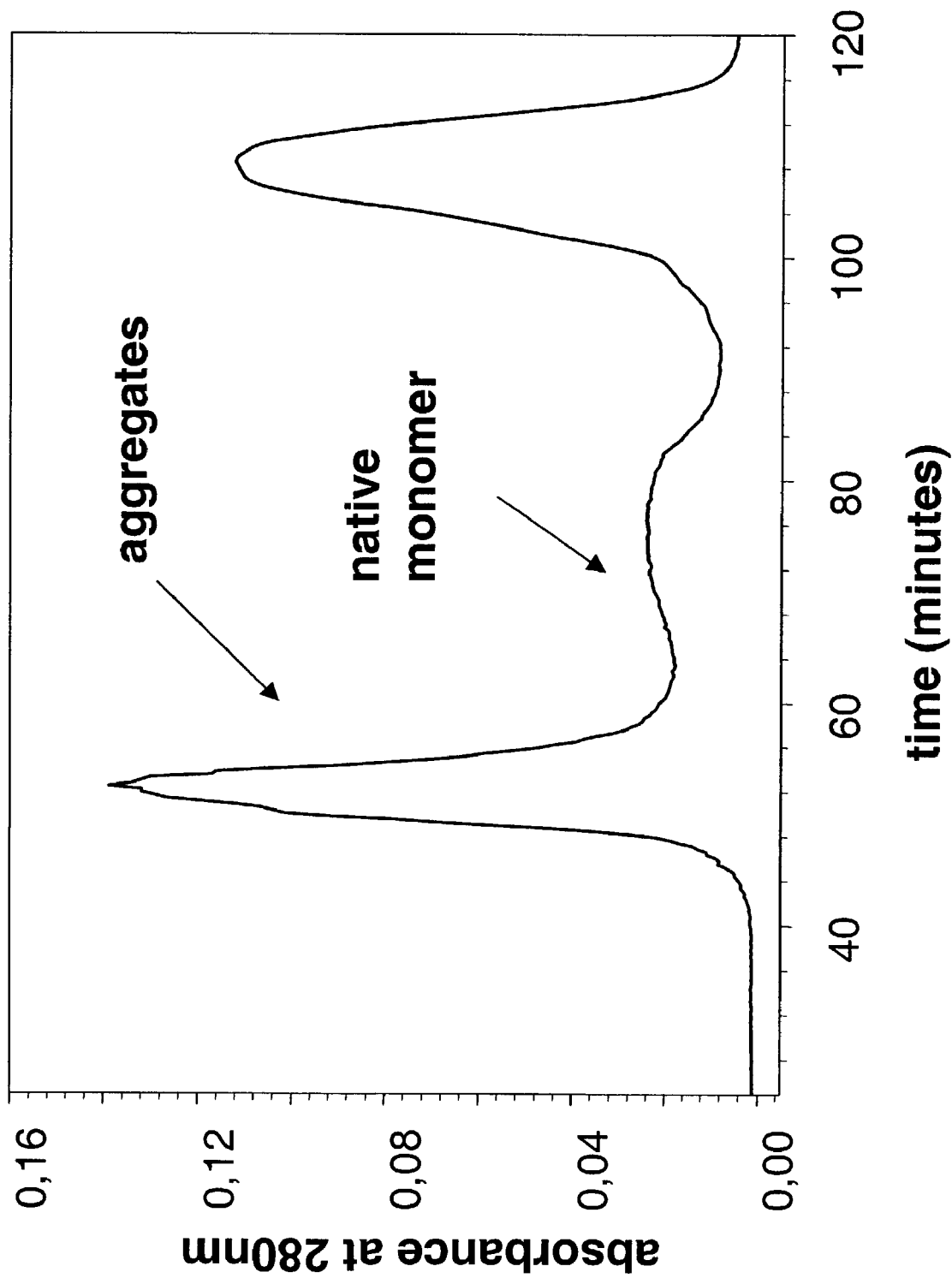

Refolding of the protein was done by matrix assisted refolding using gel-permeation chromatography. The column was equilibrated with PBS (pH 7.4) at a linear velocity of 11 cm/h. 1 ml of the feed solution was loaded onto a column with 2.6 cm i.d. and 26 cm length packed with Sephacryl 200HR. While passing through the column the chaotropic and reducing components were separated from rHuAFP and the protein started to refold (see FIG. 5, which shows matrix-assisted refolding of rHuAFP on Sephacryl 200HR).

After refolding, only 20% of the protein are in the native conformation, the remaining protein consists of stable folding intermediates resulting from non-native disulfide bridges and irreversible aggregates. The fractions were collected and analyzed by SDS-PAGE and Western-blot.

In the next step, the protein was captured by ion-exchange chromatography (Q-Sepharose XL).

Figure 6:
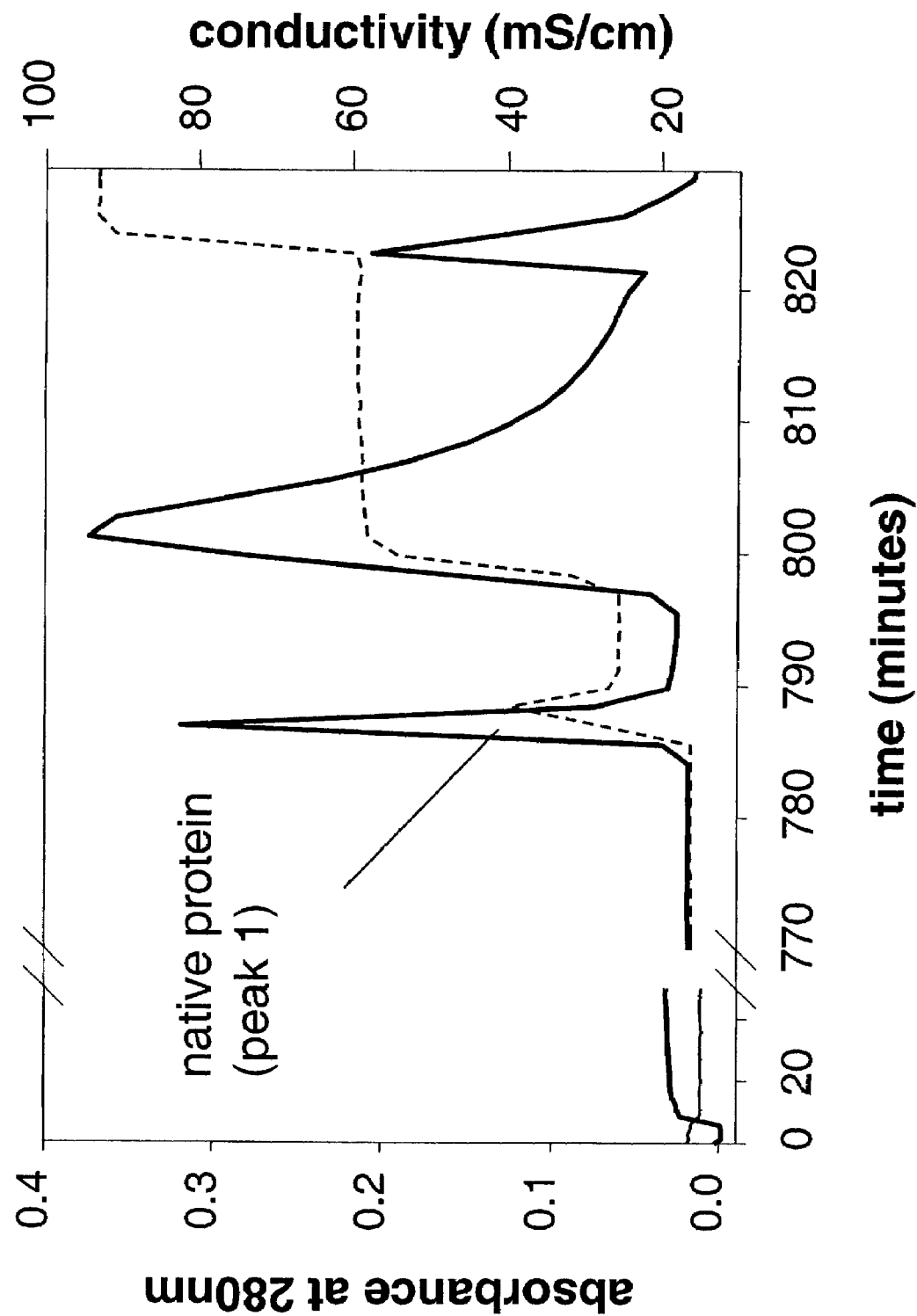
Figure 7:
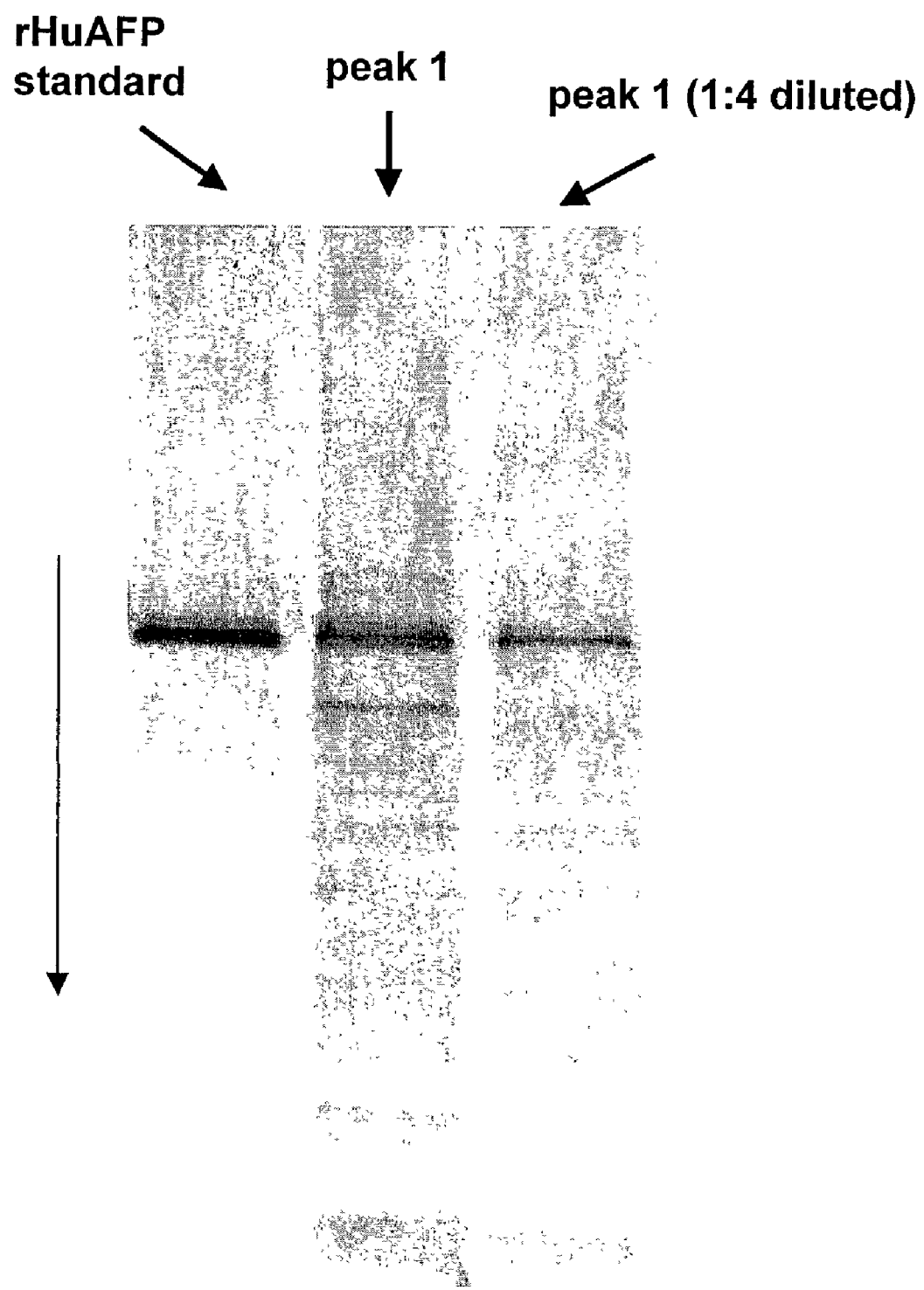
Figure 8:
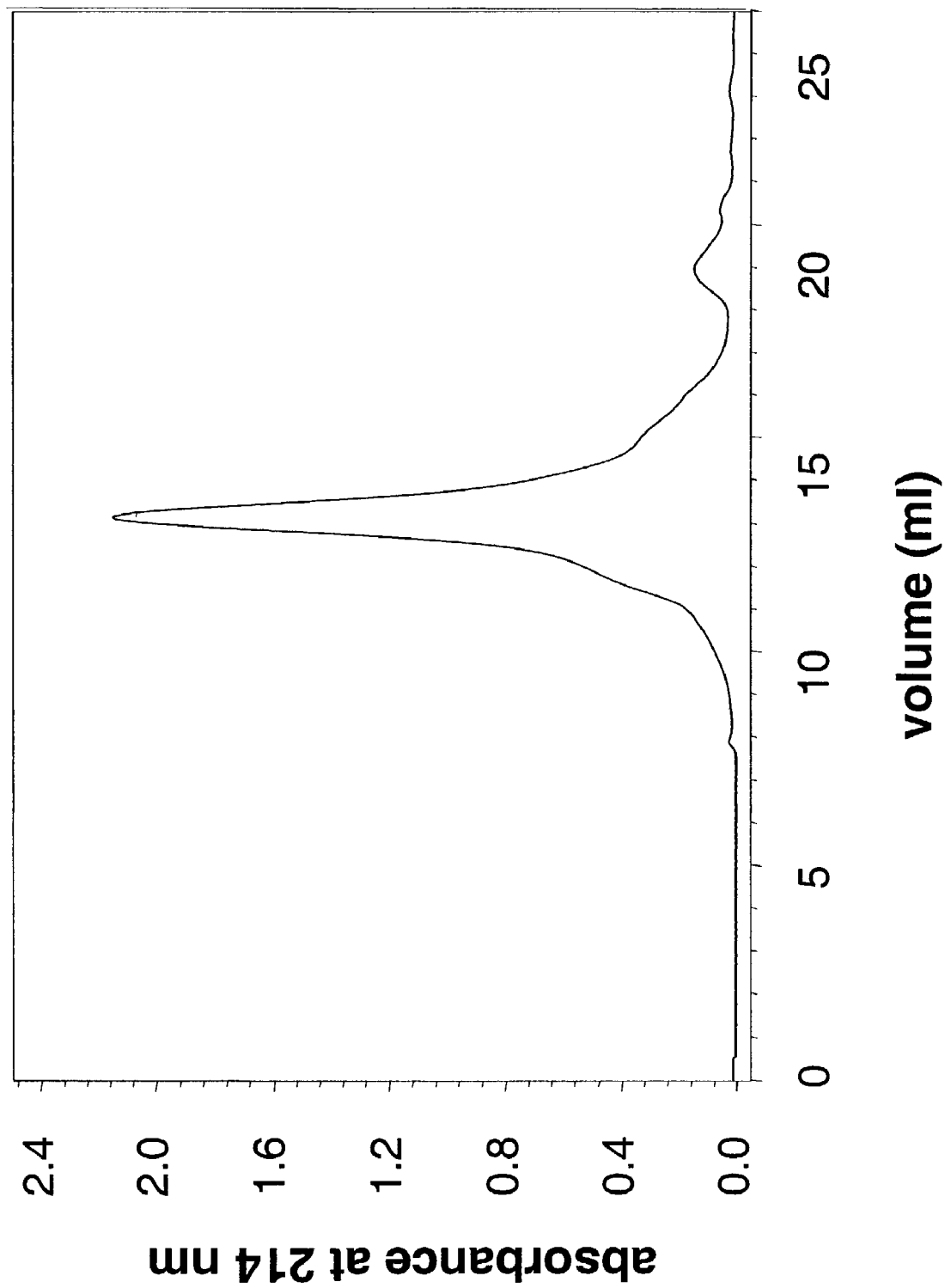

The collected protein fractions were loaded onto an Q-Sepharose XL column (10 mm i.d., 50 mm height) equilibrated with PBS. Folding intermediates did not interact with the matrix and eluted in the flow through, native rHuAFP was bound onto the resin and eluted in a step gradient with PBS+0.2M NaCl, and aggregates were eluted in a second step gradient with PBS+0.5M NaCl. The chromatogram of the capture step is shown in FIG. 6. The collected native peak fraction (eluate 1) was analyzed by silver-stained SDS-PAGE (FIG. 7) and analytical size exclusion chromatography using a Superdex 200HR column (AP biotech, Uppsala, Sweden) (FIG. 8).

b) For the continuous refolding experiments, the same protein solutions, gels and buffers were used as in a).

Two chromatographic media were packed into a annular chromatography System, PCAC from Prior Separation Technology Götzis, Austria. The lower layer consists of 5 cm Q-Sepharose XL and the upper layer of 35 cm Sephacryl 200HR.

The system was equilibrated with PBS at a linear velocity of 20 cm/h. The rotation speed of the cylinder was 250°/h.

The feed stream was pumped at the top of the gel bed through a fixed feed nozzle, whose tip was located within the layer of the glass beads. PBS+0.2M NaCl was pumped by another nozzle with a shift of −60 degrees from the feed-nozzle on the top of the gel bed.

In the first gel layer (Sephacryl 200HR) the denaturated and reduced protein started to refold. High molecular weight aggregates were separated from refolded monomeric native rHuAFP and monomeric folding intermediates. After leaving the first gel layer the proteins were captured in the second lower gel layer (Q-Sepharose XL). Native monomeric rHuAFP was eluted continuously with PBS+0.2M NaCl and aggregates were eluted in the salt fraction containing 6M GuHCl and 0.1M DTT.

Samples were drawn and the amount of aggregated protein and native protein were determined by SDS-PAGE.

Example 5

Continuous Refolding of α-lactalbumin by Ion-exchange Chromatography a) Conditions for Refolding of the Model Protein α-lactalbumin by Ion Exchange Chromatography Conditions for refolding of the model protein α-lactalbumin by ion exchange chromatography were optimized in batch mode. A column (0.5 cm i.d.) was packed with DEAE Sepharose 4FF (AP biotech, Uppsala, Sweden). The resulting bed height was 8 cm, which was approximately in the same range as used for the continuous mode. The equilibration buffer was 20 mM Tris/HCl, 2 mM $CaCl_2$, 2M urea adjusted to pH 8. The elution buffer was the same as the equilibration buffer, supplemented with 0.5M NaCl. As regeneration buffer, either 6M GuHCl containing 100 mM monothioglycerol or 0.5M NaOH was used.

A total amount of 3 mg of denatured and reduced α-lactalbumin was loaded onto DEAE Sepharose 4FF. After washing out the denaturing and reducing agents, the protein was eluted. The collected pool, containing reduced alpha-lactalbumin, was supplemented with cysteine and cystine to final concentrations of 2 mM, respectively. After incubation for 6–7 hours in the refolding buffer, about 80% of the initially loaded protein are in native conformation. Under these conditions, the total protein recovery was 90–100%.

Alternatively, 2 mM cystine and 2 mM cysteine were added to the equilibration and elution buffers. In this case, protein was eluted in its native conformation. The yield of native protein was about 10% and the recovery 80%. In order to simulate conditions required for the continuous process, restrictions concerning flow rate and amount of sample load have been made.

b) Continuous Refolding without Recycling of Aggregates

Figure 9:
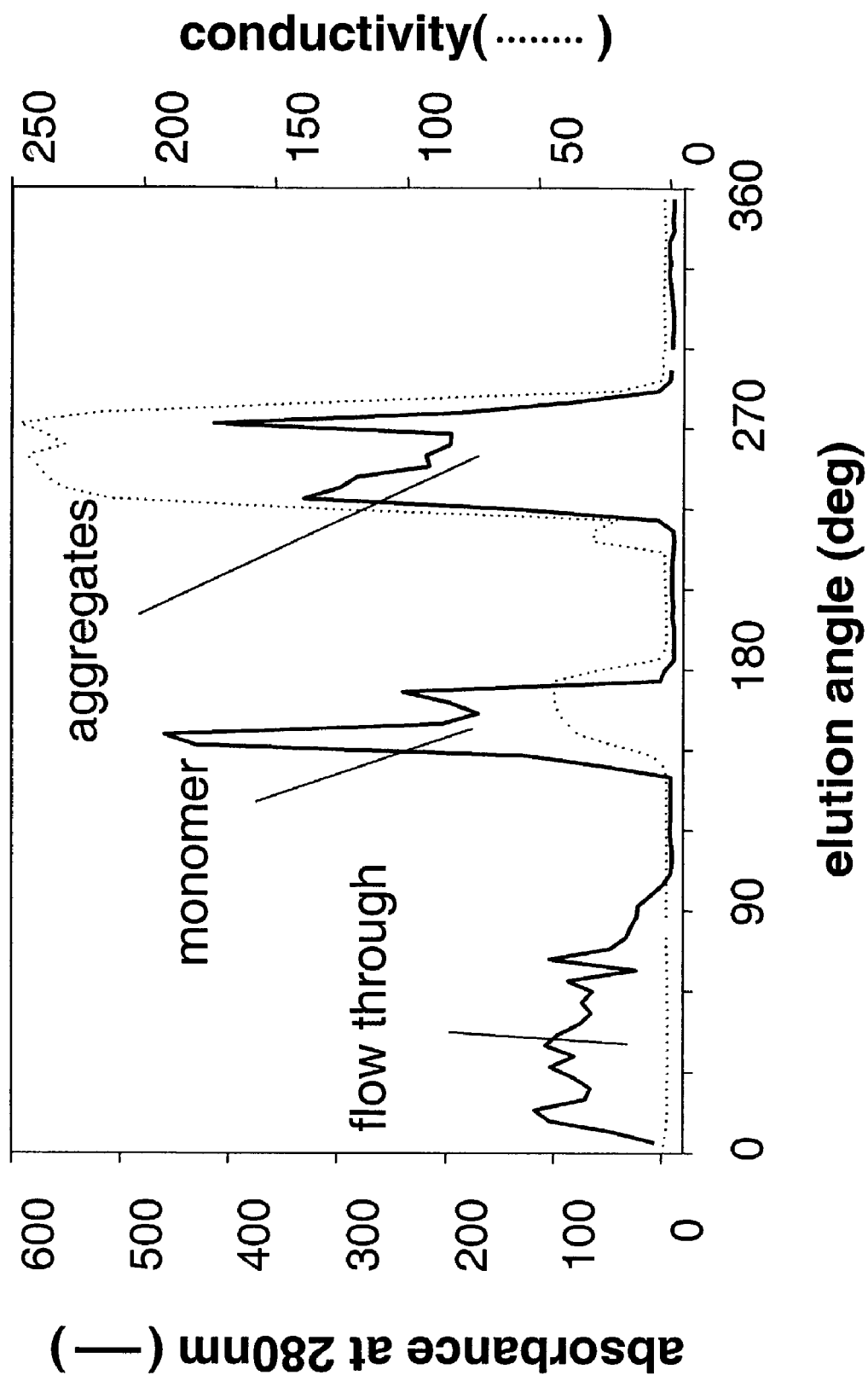

Parameters for the continuous mode were maintained as used in batch experiments. Flow velocities of the different buffers and the angles for application of the buffers were calculated. Solutions of 0.1 mg/ml and 1 mg/ml denatured and reduced α-lactalbumin were applied to the pressurized continuous annular chromatograph (PCAC) packed with DEAE Sepharose 4FF. The equilibration buffer (20 mM Tris/HCl, 2 mM $CaCl_2$, 2M urea) was pumped with a P-6000 (AP biotech, Uppsala, Sweden) at a flow rate of 22 ml/min through the main inlet port. The load was applied at 0° at a flow rate of 4.2 ml/min with a P-500 pump (AP biotech, Uppsala, Sweden). Elution was effected at 135° with elution buffer (20 mM Tris/HCl, 2 mM $CaCl_2$, 2M urea, 0.5M NaCl) at a flow rate of 2.1 ml/min with a P-500 pump (AP biotech, Uppsala, Sweden). The regeneration solution (6M GuHCl, 100 mM monothioglycerol) was pumped with a peristaltic laboratory pump at a flow rate of 1.5 ml/min at 222° into the annular chromatograph. After reaching steady state equilibrium, all 90 fractions have been collected two times for 20 minutes. The conductivity was determined and UV adsorption was measured with an external photometer (Hitachi). A representative chromatogram is shown in FIG. 9.

The fractions in which the protein eluted were determined and samples were taken. An aliquot of 200 mM cysteine and 200 mM cystine stock solutions were added to each fraction to a final concentration of 2 mM. After incubation for 7 hours, the protein content and the folding conformation was determined by reversed phase HPLC. The yield and recovery of native protein was 80% and 95%, respectively.

c) Continuous Refolding with Recycling of Aggregates

Refolding of the model protein can be accelerated by adding the 2 mM cysteine and 2 mM cystine to the equilibration and elution buffer. The protein regains its native structure during chromatography. Due to faster refolding kinetics, aggregation takes place either to a greater extend on the column. Under these conditions, the protein elutes from the column in its native state. However, most of the protein aggregates during chromatography. The aggregates can be quantitatively removed from the column with 6M GuHCl containing 100 mM monothioglycerol as reducing agent. In order to recycle the dissolved aggregates back to the ion exchange resin, the conductivity has to be below 1 mS/cm. Therefore, the dissolved aggregates have to be diafiltrated against 8M urea.

A 0.1 mg/ml and 0.5 mg/ml solution of denatured and reduced α-lactalbumin was loaded. Regeneration was effected with 6M GuHCl containing 100 mM monothioglycerol as reducing agent. All 90 fractions were collected to determine the fractions containing eluate and regenerate. The fractions containing the regenerate were pooled and diafiltrated against 8M urea until the conductivity was the same as in the feed solution. Ultradifiltration was effected with an tangential flow laboratory ultrafiltration unit (Labscale TFF system, Millipore). Final protein content was determined with reversed phase HPLC. Finally, the diafiltrate was pumped into the feed solution. The yield of native protein increases from 14% without recycling to 78% with recycling of the aggregated protein fraction.

What is claimed is:

1. A method for obtaining a biologically active recombinant protein comprising subjecting a feed solution containing a recombinant protein of interest in its denatured form and/or in biologically inactive intermediate forms to a continuous or quasi-continuous chromatographic separation process, wherein said protein is reconstituted under conditions that promote refolding of said protein and said denatured form and said intermediate forms of said protein are separated from the refolded protein.

2. The method of claim 1, wherein said intermediate forms that have been separated from said refolded protein are added to the feed solution and thus undergo at least one more reconstitution process.

3. The method of claim 2, wherein said separation process is selected from the group consisting of ion-exchange chromatography, affinity chromatography, hydrophobic interaction chromatography, reversed phase chromatography, covalent chromatography, size exclusion chromatography and adsorption chromatography.

4. The method of claim 3, wherein said separation process is operated continuously in the form of annular chromatography.

5. The method of claim 3, wherein said separation process is operated quasi-continuously in the form of a simulated moving bed chromatography.

6. The method of claim 3, wherein said separation process is operated quasi-continuously in the form of a carrousel chromatography.

7. The method of claim 1, wherein a regeneration solution is applied to a bed used in said chromatographic separation process.

8. The method of claim 7, wherein said regeneration solution is selected from the group consisting of a strong alkaline solution, a strong acidic solution, a chaotropic buffer, an organic solvent, an aqueous buffer supplemented with an organic solvent, and an aqueous buffer with an ionic or non-ionic detergent.

9. The method of claim 7, wherein said regenerating solution exits said chromatographic separation process and contains greater than or equal to 10% of intermediate forms of said protein.

10. The method of claim 9, wherein said regenerating solution containing said intermediate forms of said protein is recycled to said chromatographic separation process.

11. The method of claim 10, wherein said regenerating solution containing said intermediate forms of said protein is concentrated and/or diafiltrated before said regenerating solution is added to said feed solution.

12. The method of claim 4, wherein a chromatographic medium is perfused with a refolding buffer.

13. The method of claim 4, wherein an eluent containing a refolding buffer is introduced continuously at the top of a bed used in said annular chromatography.

14. The method of claim 4, wherein said biologically active protein and said intermediate forms of said protein elute at different exit points in an exit stream.

15. The method of claim 14, wherein said intermediate forms are concentrated before said intermediate forms are added to said feed solution.

16. The method of claim 12, wherein fractions of said protein that are not refolded are separated from the refolded protein during said adsorption.

17. The method of claim 13, wherein said protein fractions that are not refolded are added to said feed solution.

18. The method of claim 16, wherein said completely or partially refolded protein is desorbed under conditions that favor refolding.

19. The method of claim 18, wherein said completely or partially refolded protein is desorbed while maintaining its native conformation.

20. The method of claim 3, wherein said separation process is adsorption chromatography and at least a fraction of said denatured form of said protein completely or partially refolds during adsorption in the presence of refolding buffer.

21. The method of claim 20, wherein fractions of said protein that are not refolded are separated from the refolded protein during said desorption.

22. The method of claim 20, wherein said protein fractions that are not refolded are added to said feed solution.

23. The method of claim 4, wherein a regeneration solution is applied to a bed used in said annular chromatography at a position that is sufficiently distant from a feed inlet position of said annular chromatography to avoid mixing said regeneration solution and said feed solution.

24. The method of claim 23, wherein said regeneration solution elutes at a position different from eluate containing said intermediate forms of said protein and eluate containing said refolded protein.

25. The method of claim 24, wherein said regeneration solution is recycled to said chromatographic separation process by combining said regeneration solution with said feed solution.

26. The method of claim 24, wherein said regeneration solution is recycled to said chromatographic separation process by combining said regeneration solution with said eluate containing said intermediate forms of said protein.

27. The method of claim 4, wherein an eluate stream has a concentration of said protein that is constant over time.

28. The method of claim 3, wherein said feed solution is diluted with a solution containing said added intermediate forms of said protein.

29. The method of claim 28, wherein said separation process is selected from the group consisting of ion exchange chromatography and adsorption chromatography.

30. The method of claim 3, wherein said separation process occurs in a column and said feed solution does not exceed one-third of the volume of said column.

31. The method of claim 30, wherein said intermediate forms are concentrated after they are eluted.

32. The method of claim 31, wherein said separation process is size exclusion chromatography.

33. The method of claim 5, wherein an eluate stream has a concentration of said protein that changes cyclically over time.

* * * * *